(12) United States Patent
Smith et al.

(10) Patent No.: US 8,129,132 B2
(45) Date of Patent: Mar. 6, 2012

(54) DETECTION OF AUTOANTIBODIES REACTIVE WITH PANCREATIC ISLET CELL ANTIGENIC MOLECULES AND/OR INSULIN

(75) Inventors: Bernard Rees Smith, Cardiff (GB); Jadwiga Furmaniak, Cardiff (GB); Michael Powell, Cardiff (GB)

(73) Assignee: RSR Limited, Cardiff (GB)

( * ) Notice: Subject to any disclaimer, the term of this patent is extended or adjusted under 35 U.S.C. 154(b) by 694 days.

(21) Appl. No.: 10/496,528

(22) PCT Filed: Nov. 26, 2002

(86) PCT No.: PCT/GB02/05285
§ 371 (c)(1),
(2), (4) Date: Sep. 21, 2004

(87) PCT Pub. No.: WO03/048772
PCT Pub. Date: Jun. 12, 2003

(65) Prior Publication Data
US 2005/0019837 A1    Jan. 27, 2005

(30) Foreign Application Priority Data
Nov. 28, 2001 (GB) ................................. 0128583.2

(51) Int. Cl.
*G01N 33/538* (2006.01)
*G01N 33/543* (2006.01)
*G01N 33/564* (2006.01)
*G01N 33/573* (2006.01)

(52) U.S. Cl. ........ 435/7.4; 435/7.94; 436/506; 436/518; 436/541

(58) Field of Classification Search .................. None
See application file for complete search history.

(56) References Cited

U.S. PATENT DOCUMENTS 5,200,318 A * 4/1993 Rabin et al. ................. 435/7.21
(Continued)

FOREIGN PATENT DOCUMENTS

EP          0569800       11/1993
(Continued)

OTHER PUBLICATIONS

The Merck Manual, Seventeenth Edition, Merck Research Laboratories, 1999, p. 1497.*

(Continued)

*Primary Examiner* — David A Saunders
(74) *Attorney, Agent, or Firm* — Merchant & Gould P.C.

(57) ABSTRACT

A method of screening a sample of body fluid obtained from an animal subject for analyte autoantibodies reactive with one or more antigenic molecules selected from pancreatic islet cell antigenic molecules and insulin, or one or more variants, analogues, derivatives or fragments thereof, and a kit for use in such a method.

6 Claims, 2 Drawing Sheets

U.S. PATENT DOCUMENTS

Figure 1A:
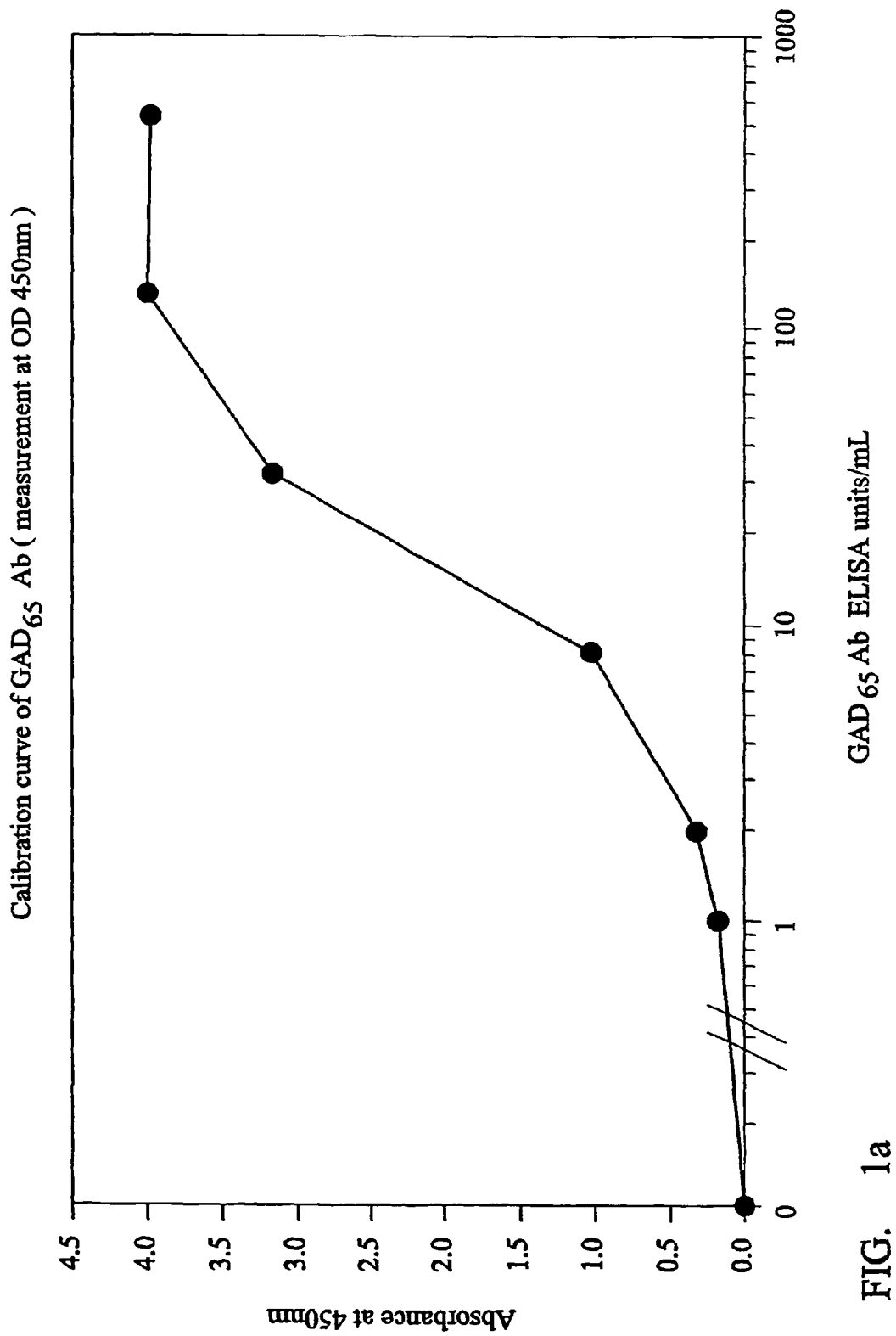

| | | | |
|---|---|---|---|
| 5,849,506 A | * | 12/1998 | Baekkeskov et al. ......... 435/7.4 |
| 5,908,627 A | * | 6/1999 | Pietropaolo et al. ....... 424/152.1 |
| 6,187,563 B1 | * | 2/2001 | Solimena et al. ........... 435/69.1 |

FOREIGN PATENT DOCUMENTS

| | | |
|---|---|---|
| EP | 0902286 | 3/1999 |
| WO | 88/09933 | 12/1988 |

OTHER PUBLICATIONS

Couzin, "Diabetes' Brave New World" Science, vol. 300, 1862-1865, 2003.*

Wolk, et al., "Association between High Concentration of Antibodies to Insulin and Some Diseases Common to Elderly", Gerontology 1993; 39: 334-337.

Atkinson, et al., "Type I Diabetes: new perspectives on disease pathogenesis and treatment", Lancet 2001; 358: 221-229.

Grubin, et al., "A novel radioligand binding assay to determine diagnostic accuracy of isoform-specific glutamic acid decarboxylase antibodies in childhood IDDM", Diabetologia 1994; 37: 344-350.

Peterson, et al., "Detection of GAD65 Antibodies in Diabetes and Other Autoimmune Diseases Using a Simple Radioligand Assay", Diabetes 1994; 43: 459-467.

Falomi, et al., "Radioimmunoassays for glutamic acid decarboxylase (GAD65) and GAD65 autoantibodies using 35S or 3H recombinant human ligands", Journal of Immunological Methods 1995; 186: 89-99.

Rowley, et al., "Antibodies to Glutamic Acid Decarboxylase Discriminate Major Types of Diabetes Mellitus", Diabetes 1992; 41: 548-551.

Ohta, et al., "A Simple Solid-Phase Radioimmunoassay for Glutamic Acid Decarboxylase (GAD) Antibodies in Patients with Diabetes Mellitus", Journal of Clinical Biochemical Nutrition 1996; 20: 139-148.

Lühder, et al., "Detection of autoantibodies to the 65-kD isoform of glutamate decarboxylase by radioimmunoassay", European Journal of Endocrinology 1994; 130: 575-580.

Powell, et al., "Glutamic acid decarboxylase autoantibody assay using 125I-labelled recombinant GAD65 produced in yeast", Clinica Chimica Acta 1996; 256: 175-188.

Matsuba, et al., "Expression of Recombinant Human Glutamic Acid Decarboxylase (GAD) in Myeloma Cells and Enzyme-Linked Immunosorbent Assay (ELISA) for Autoantibodies to GAD", Journal of Biochemistry 1997; 121: 20-24.

Zavialov, et al., "Novel fusion proteins in the analysis of diabetes-associated autoantibodies to GAD65 and IA-2", Journal of Immunological Methods 2000; 246: 91-96.

Rickert, et al., "Fusion Proteins for Combined Analysis of Autoantibodies to the 65-kDa Isoform of Glutamic Acid Decarboxylase and Islet Antigen-2 in Insulin-dependent Diabetes Mellitus", Clinical Chemistry 2001; 47: 926-934.

Gronowski, et al., "Detection of Glutamic Acid Decarboxylase Autoantibodies with the varelisa ELISA", Clinical Chemistry 1995; 41: 1532-1534.

Mehta, et al., "DELISA: sensitive nonisotopic assay for GAD65 autoantibodies, a key risk-assessment marker for insulin-dependent diabetes mellitus", Clinical Chemistry 1996; 42: 263-269.

Schmidli, et al., "Disease Sensitivity and Specificity of 52 Assays for Glutamic Acid Decarboxylase Antibodies", Diabetes 1995; 44: 636-640.

5th Internation Congress of the Immunology of Diabetes Society, "Abstracts", Diabetes/Metabolism: Research and Reviews 2001; 17: S25, abstract No. 020.

Masuda, et al., "Autoantibodies to IA-2 in insulin-dependent diabetes mellitus: Measurements with a new immunoprecipitation assay", Clinica Chimica Acta 2000; 291: 53-66.

Lernmark, 1999, Clinical Chemistry, vol. 45:8(B), pp. 1331-1338 "Type I Diabetes."

Liu et al., 2007, Clinical Immunology, vol. 125, pp. 120-126 "Accepting clocks that tell time poorly: Fluid-phase versus standard ELISA autoantibody assays."

Pfützner et al., 1995, Endocrinology & Diabetes, pp. 123-125 "Determination of anti GAD65 autoanitbodies with an ELISA before and after standardization with new international reference serum."

Schmidli et al., Aug. 1994, Diabetes, vol. 43, pp. 1005-1009 "High Level of Concordance Between Assays for Glutamic Acid Decarboxylase Antibodies: The First International Glutamic Acid Decarboxylase Antibody Workshop."

Verge et al., Dec. 1998, Diabetes, vol. 47, pp. 1857-1866 "Combined Use of Autoantibodies (IA-2 Autoantibody, GAD Autoantibody, Insulin Autoantibody, Cytoplasmic Islet Cell Antibodies) in Type 1 Diabetes."

Wild et al., 1997, Horm. Metab. Res. 29, pp. 403-406 Comparison of New Anti-glutamic Decarboxylase (GAD) Enzyme-Linked Immunosorbent Assay (ELISA) with Radioimmunoassay Methods: A Multicenter Study.

Table 1, Comparison of the $GAS_{65}$ autoantibody ELISA according to the present invention, a standard $GAD_{65}$ autoantibody ELISA (based on alkaline phosphatase labelled anti human IgG) manufactured by Biomerica and a RIA based on $^{125}$I-lablled $GAD_{65}$, 1 page.

Brooking et al., 2003, "A sensitive non-isotopic assay for $GAD_{65}$ autoantibodies." Clinica Chimica Acta 331, pp. 55-59.

Biomerica, Isletest-GAD, Ref. 7009, "Qualitative ELISA test for the detection of circulating autoantibodies against GAD antigens." 4 pages.

RSR Limited, 2007, "Glutamic Acid Decarboxylase (GAD) Autoantibody RIA kit from RSR—Instructions for use." 4 pages.

Biomerica, Isletest-GAD, Ref. 7011, "Qualitative ELISA test for the detection of circulating autoantibodies against against human insulin." 4 pages.

Biomerica, Isletest-GAD, Ref. 7010, "Qualitative ELISA test for the detection of circulating autoantibodies against islet cell antigens." 4 pages.

Coco et al., "Analysis of the $GAD_{65}$-$GAD_{65}$ autoantibody interaction." Clinica Chimica Acta 391, 2008, pp. 51-59.

* cited by examiner

DETECTION OF AUTOANTIBODIES REACTIVE WITH PANCREATIC ISLET CELL ANTIGENIC MOLECULES AND/OR INSULIN

The present invention relates to methods and kits useful in the detection of autoantibodies reactive with pancreatic islet cell antigenic molecules and/or insulin, for example methods and kits useful in the detection of autoantibodies indicative of the onset or presence of insulin dependent diabetes mellitus (IDDM, type 1 diabetes).

Type 1 diabetes is one of the more prevalent autoimmune diseases affecting man, with more than 2 million individuals in Europe and North America suffering from the disease (M A Atkinson, G S Eisenbarth. Type 1 diabetes: new perspectives on disease pathogenesis and treatment. The Lancet, 2001 358: 221-229). Furthermore, the incidence of type 1 diabetes is increasing worldwide by 2.5% per year and it is estimated that the incidence of this disease will be 40% higher in 2010 that in 1998 (M A Atkinson, G S Eisenbarth. Type 1 diabetes: new perspectives on disease pathogenesis and treatment. The Lancet, 2001 358: 221-229).

Autoantibodies to pancreatic β cell antigens are well recognised serological markers of type 1 diabetes and these include: autoantibodies reactive with islet cells in immunofluorescence tests (ICA), autoantibodies to glutamic acid decarboxylase (GAD, in particular the 65 kDa isoform thereof, $GAD_{65}$), autoantibodies to protein tyrosine phosphatase-like islet cell antigen (which can be referred to as IA-2 or ICA512) and autoantibodies to insulin. $GAD_{65}$ autoantibodies and IA-2 autoantibodies are components of ICA reactivity (M A Atkinson, G S Eisenbarth. Type 1 diabetes: new perspectives on disease pathogenesis and treatment. The Lancet, 2001 358: 221-229). At least one of the three types of autoantibodies to $GAD_{65}$, IA-2 and insulin are present at diagnosis in sera from about 90% of patients with type 1 diabetes (M A Atkinson, G S Eisenbarth. Type 1 diabetes: new perspectives on disease pathogenesis and treatment The Lancet, 2001 358: 221-229). Measurement of the above mentioned autoantibodies being serological markers of autoimmunity to pancreatic β cells can also be useful in monitoring patients involved in trials for prevention of diabetes (M A Atkinson, G S Eisenbarth. Type 1 diabetes: new perspectives on disease pathogenesis and treatment. The Lancet, 2001 358: 221-229).

Currently, $GAD_{65}$ autoantibodies are measured using immunoprecipitation assays (IPA) employing $GAD_{65}$ radioactively labelled with $^{35}S$, $^{3}H$ or $^{125}I$. $GAD_{65}$ labelled with $^{35}S$ or $^{3}H$ has been produced in an in vitro transcription/translation system (C E Grubin, T Daniels, B Toivola, M Landdin-Olsson, W A Hagopian, L Li, A E Karlsen, E Boel, B Michelsen, Å Lernmark. A novel radioligand binding assay to determine diagnostic accuracy of isofoan-specific glutamic acid decarboxylase antibodies in childhood IDDM. Diabetologia, 1994 37: 344-350; J S Petersen, K R Hejnaes, A Moody, A E Karlsen, M O Marshall, M Høier-Madsen, E Boel, B K Michelsen, T Dyrberg. Detection of $GAD_{65}$ antibodies in diabetes and other autoimmune diseases using a simple radioligand assay. Diabetes, 1994 43: 459-467; and A Falorni, E Örtqvist, B Persson, Å Lernmark. Radioimmunoassays for glutamic acid is decarboxylase ($GAD_{65}$) and $GAD_{65}$ autoantibodies using $^{35}S$ or $^{3}H$ recombinant human ligands. Journal of Immunological Methods, 1995 186: 88-89). Native $GAD_{65}$, for example rat or porcine $GAD_{65}$ isolated from brain tissue (M J Rowley, I R Macklay, Q-Y Chen, W J Knowles, P Z Zimmet. Antibodies to glutamic acid decarboxylase discriminate major types of diabetes mellitus. Diabetes, 1992 41: 548:551; and M Ohta, H Obayashi, K Takahashi, Y Kitagawa, K Nakano, S Matsuo, M Ohishi, N Itoh, K Hayashi, K Ohta. A simple solid-phase radioimmunoassay for glutamic acid decarboxylase (GAD) antibodies in patients with diabetes mellitus. J Clin Biochem Nutr, 1996 20: 139-148) or recombinant human $GAD_{65}$, for example expressed in insect cells, yeast or mammalian cells (F Lühder, K-P Woltanski, L Mauch, H Haubruck, K-D Kohnert, I Rjasanowski, D Michaelis, M Ziegler. Detection of autoantibodies to the. 65-kD isoform of glutamate decarboxylase by radioimmunoassay. European Journal of Endocrinology, 1994 130: 575-80; M Powell, L Prentice, T Asawa, R Kato, J Sawicka, H Tanaka, V Petersen, A Munkley, S Morgan, B Rees Smith, J Furmaniak. Clinica Chimica Acta, 1996 256: 175-188; and T Matsuba, M Yano, No Abiru, H Talkino, S Akazawa, S Nagataki, K Yasukawa Expression of recombinant human glutamic acid decarboxylase (GAD) in myeloma cells and enzyme-linked immunosorbent assay (ELISA) for autoantibodies to GAD. J Biochem, 1997 121: 2024)have been labelled with $^{125}I$ and used in IPAs. Recombinant fusion proteins of $GAD_{65}$ and IA-2 have also been used in IPAs for combined autoantibody testing (A Zavialov, M Ankelo, A Westerlund-Karlsson, M Knip, J Illonen, A Hinkkanen. Novel fusion proteins in the analysis of diabetes associated autoantibodies to $GAD_{65}$ and IA-2. Journal of Immunological Methods, 2000 246: 91-96; and M Rickert, J Seissler, W Dangel, H Lorenz, W Richter. Fusion proteins for combined analysis of autoantibodies to the 65-kDa isoform of glutamic acid decarboxylase and islet antigen-2 in insulin dependent diabetes mellitus. Clinical Chemistry, 2001 47(5):926-934).

Currently available IPAs based on $^{35}S$-$GAD_{65}$ have, however, been technically demanding, difficult to standardise, relatively expensive and have not been adaptable to a kit format. Assays based on human recombinant $^{125}I$-$GAD_{65}$ have been of equal sensitivity and specificity to assays based on $^{35}S$-$GAD_{65}$, and have exhibited the added advantage of good reproducibility, technical simplicity, lower costs and have been easily adapted into a kit. Unfortunately, however, assays based on $^{125}I$-$GAD_{65}$ isolated from rat or porcine brain tissue have suffered from lower specificity due to contamination with $GAD_{67}$ isoform.

$GAD_{65}$ autoantibodies have also been measured by different types of ELISAs (A M Gronowski, E C C Wong, T R Wilhite, D L Martin, C H Smith, C A Parvin, M Landt. Detection of glutamic acid decarboxylase autoantibodies with the varelisa ELISA. Clinical Chemistry, 1995 41(10): 1532-1534; and H D Mehta, B S Vold, S Minkin, E F Ullman. DELISA: sensitive nonisotopic assay for $GAD_{65}$ autoantibodies, a key risk-assessment marker for insulin-dependent diabetes mellitus. Clinical Chemistry, 1996 42(2): 263-269).

However, currently available tests to measure $GAD_{65}$ autoantibodies by ELISA have poorer sensitivity and specificity than the above mentioned IPAs and do not compare well with the IPAs in proficiency studies (R S Schmidli, P G Colman, E Bonifacio, Participating Laboratories. Disease sensitivity and specificity of 52 assays for glutamic acid decarboxylase antibodies. The second international GADAb workshop. Diabetes, 1995 44: 636-640).

The present invention, however, alleviates the problems hitherto associated with methods and kits employed in the screening of autoantibodies indicative of the onset or presence of type 1 diabetes and have general applicability in the detection of autoantibodies reactive with pancreatic islet cell antigenic molecules and/or insulin. In particular, the present invention employs methods and kits having improved specificity and sensitivity when compared to prior art techniques as discussed above.

There is provided by the present invention a method of screening a sample of body fluid obtained from an animal subject for analyte autoantibodies reactive with one or more antigenic molecules selected from pancreatic islet cell antigenic molecules and insulin, or one or more variants, analogues, derivatives or fragments thereof, said method comprising:

(a) providing said sample of body fluid from said subject;
(b) providing one or more first sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof;
(c) providing one or more second sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof;
(d) contacting said antigenic molecules as provided by steps (b) and (c) simultaneously or successively with said sample of body fluid being screened, whereby analyte autoantibodies when present in said sample of body fluid can interact with said antigenic molecules so as to form one or more complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule;
(e) prior to, or concurrent with, or subsequent to, step (d), providing immobilising means whereby said antigenic molecule of said first source as present in a complex as formed in step (d) is immobilised to a solid support prior to, or concurrent with, or subsequent to, step (d);
(f) prior to, or concurrent with, or subsequent to, step (d), providing direct or indirect detectable labelling means whereby said antigenic molecule of said second source as present in a complex as formed in step (d) is provided with such direct or indirect detectable labelling means prior to, or concurrent with, or subsequent to, step (d); and
(g) detecting the presence of complexes formed in (d) immobilised according to (e) so as to provide an indication of analyte autoantibodies present in said sample.

A method of screening for analyte autoantibodies according to the present invention is particularly advantageous in providing a method for such autoantibody detection of high specificity and sensitivity.

The one or more antigenic molecules, or one or more variants, analogues, derivatives or fragments thereof, or fusion molecules thereof, that can react with analyte autoantibodies as required by the present invention can be selected from any pancreatic islet cell antigenic molecule and insulin, and one or more variants, analogues, derivatives or fragments thereof, or fusion molecules thereof and in particular can suitably be selected from the group consisting of glutamic acid decarboxylase (GAD, and in particular the 65 KDa and 67 KDa isoforms of glutamic acid decarboxylase, $GAD_{65}$ and $GAD_{67}$), protein tyrosine phosphatase-like islet cell antigen (IA-2) and insulin, or one or more variants (such as, for example, IA-2 beta), analogues, derivatives or fragments thereof, or fusion molecules comprising two or more of the above, with which analyte autoantibodies when present in said sample of body fluid can interact. In a particularly, preferred embodiment of the present invention, one or more of the above mentioned pancreatic islet cell antigenic molecules or insulin are employed, in particular the above mentioned pancreatic islet cell antigenic molecules, preferably one or more of $GAD_{65}$, $GAD_{67}$ or IA-2. Alternatively it may be preferred that one or more variants, analogues, derivatives or fragments of one or more of the above mentioned pancreatic islet cell antigenic molecules or insulin are employed, in particular one or more variants, analogues, derivatives or fragments of the above mentioned pancreatic islet cell antigenic molecules, preferably one or more variants, analogues, derivatives or fragments of one or more of $GAD_{65}$, $GAD_{67}$ or IA-2. In a further alternative preferred embodiment of the present invention, it may be preferred that one or more fusion molecules are employed comprising two or more directly or indirectly fused antigenic molecules selected from the above mentioned pancreatic islet cell antigenic molecules, insulin and said one or more variants, analogues, derivatives or fragments thereof It will be appreciated, therefore, that the term GAD as used herein encompasses all isoforms of GAD, including in particular $GAD_{65}$ or $GAD_{67}$ and in certain embodiments of the present invention it may be preferred that $GAD_{65}$ is employed and in other embodiments of the present invention it may be preferred that $GAD_{67}$ is employed. It will also be appreciated from the above that the present invention can include within its scope fusion molecules that can comprise $GAD_{65}$ or $GAD_{67}$, or one or more fragments thereof (such as binding regions thereof). For example, fusion molecules for use within the scope of the present invention can comprise $GAD_{65}$ directly or indirectly fused to $GAD_{67}$, or one or more binding regions of $GAD_{65}$ directly or indirectly fused to one or more binding regions or $GAD_{67}$. Furthermore, it will also be appreciated that fusion molecules for use within the scope of the present invention can comprise IA-2, or one or more binding regions thereof, directly or indirectly fused to IA-2 beta, or one or more binding regions thereof. The present invention also allows for $GAD_{65}$ or $GAD_{67}$, or one or more variants, analogues, derivatives or fragments thereof, directly or indirectly fused to IA-2, or one or more variants, analogues, derivatives or fragments thereof.

In particular the one or more antigenic molecules, or one or more variants, analogues, derivatives or fragments thereof, that can react with such analyte autoantibodies as required by the present invention, can suitably be selected from the group consisting of glutamic acid decarboxylase (in particular $GAD_{65}$ or $GAD_{67}$) and protein tyrosine phosphatase-like islet cell antigen (IA-2), or one or more variants; analogues, derivatives or fragments thereof, with which analyte autoantibodies when present in said sample of body fluid can interact.

In a preferred aspect of the present invention, therefore, a method of screening substantially as hereinbefore described is for use in detecting analyte autoantibodies to GAD and/or IA-2, and the one or more antigenic molecules comprise $GAD_{65}$ or $GAD_{67}$, or one or more variants, analogues, derivatives or fragments thereof, and/or IA-2, or one or more variants, analogues, derivatives or fragments thereof; with which analyte autoantibodies when present in said sample of body fluid can interact. In the case where fusion antigenic molecules are employed in the present invention, suitable fusion molecules may comprise $GAD_{65}$ or $GAD_{67}$ or one or more variants, analogues, derivatives or fragments thereof, directly or indirectly fused to IA-2, or one or more variants, analogues, derivatives or fragments thereof; alternatively, suitable fusion molecules may comprise $GAD_{65}$ directly or indirectly fused to $GAD_{67}$, or one or more binding regions of $GAD_{65}$ directly or indirectly fused to one or more binding regions or $GAD_{67}$; alternatively suitable fusion molecules may comprise IA-2, or one or more binding regions thereof, directly or indirectly fused to IA-2 beta, or one or more binding regions thereof.

Preferably a method according to the present invention comprises providing one or more first sources of antigenic molecules selected from $GAD_{65}$, $GAD_{67}$, IA-2, insulin, one or more variants, analogues, derivatives or fragments thereof and fusion molecules comprising two or more directly or indirectly fused antigenic molecules selected from $GAD_{65}$, $GAD_{67}$, IA-2, insulin and said one or more variants, analogues, derivatives or fragments thereof; with which analyte autoantibodies when present in said sample of body fluid can interact, immobilised to a solid support according to step (e) of a method according to the present invention and one or more second sources of antigenic molecules selected from $GAD_{65}$, $GAD_{67}$, IA-2, insulin, one or more variants, analogues, derivatives or fragments thereof and fusion molecules comprising two or more directly or indirectly fused antigenic molecules selected from $GAD_{65}$, $GAD_{67}$, IA-2, insulin and said one or more variants, analogues, derivatives or fragments thereof, with which analyte autoantibodies when present in said sample of body fluid can interact, provided with labelling means according to step (f) of a method according to the present invention.

More preferably, a method according to the present invention comprises providing one or more first sources of antigenic molecules selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2, and said one or more variants, analogues, derivatives or fragments thereof, with which analyte autoantibodies when present in said sample of body fluid can interact (for example fusion molecules comprising $GAD_{65}$, $GAD_{67}$, or one or more variants, analogues, derivatives or fragments thereof directly or indirectly fused to IA-2 or one or more variants, analogues, derivatives or fragments thereof, with which analyte autoantibodies when present in said sample of body fluid can interact), immobilised to a solid support according to step (e) of a method according to the present invention and a second source of antigenic molecules selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2, and one or more variants, analogues, derivatives or fragments thereof, with which analyte autoantibodies when present in said sample of body fluid can interact (such as fusion molecules comprising $GAD_{65}$ or $GAD_{67}$, or one or more variants, analogues, derivatives or fragments thereof directly or indirectly fused to IA-2 or one or more variants, analogues, derivatives or fragments thereof, with which analyte autoantibodies when present in said sample of body fluid can interact), provided with labelling means according to step (f) of a method according to the present invention. It may be preferred that where a method according to the present invention is required to detect autoantibodies to GAD, the method comprises providing a first source of antigenic molecules consisting essentially of GAD antigenic molecules selected from $GAD_{65}$, $GAD_{67}$, one or more variants, analogues, derivatives or fragments thereof with which analyte autoantibodies when present in said sample of body fluid can interact and fusion molecules comprising two or more directly or indirectly fused antigenic molecules selected from $GAD_{65}$, $GAD_{67}$ and the one or more variants, analogues, derivatives or fragments thereof, (such as fusion molecules comprising $GAD_{65}$ directly or indirectly fused to $GAD_{67}$, or one or more binding regions of $GAD_{65}$ directly or indirectly fused to one or more binding regions or $GAD_{67}$, with which analyte autoantibodies when present in said sample of body fluid can interact), immobilised to a solid support according to step (e) of a method according to the present invention and a second source of antigenic molecules consisting essentially of GAD antigenic molecules selected from $GAD_{65}$, $GAD_{67}$, one or more variants, analogues, derivatives or fragments thereof with which analyte autoantibodies when present in said sample of body fluid can interact and fusion molecules comprising two or more directly or indirectly fused antigenic molecules selected from $GAD_{65}$, $GAD_{67}$ and one or more variants, analogues, derivatives or fragments thereof, with which analyte autoantibodies when present in said sample of body fluid can interact (such as $GAD_{65}$ directly or indirectly fused to $GAD_{67}$, or one or more binding regions of $GAD_{65}$ directly or indirectly fused to one or more binding regions or $GAD_{67}$) provided with labelling means according to step (f) of a method according to the present invention. Alternatively, it may be preferred that where a method according to the present invention is required to detect autoantibodies to IA-2, the method comprises providing a first source of antigenic molecules consisting essentially of IA-2 antigenic molecules selected from IA-2, one or more variants, analogues, derivatives or fragments thereof, with which analyte autoantibodies when present in said sample of body fluid can interact and fusion molecules comprising two or more directly or indirectly fused antigenic molecules selected from IA-2 and one or more variants, analogues, derivatives or fragments thereof, with which analyte autoantibodies when present in said sample of body fluid can interact (such as IA-2, or one or more binding regions thereof, directly or indirectly fused to IA-2 beta, or one or more binding regions thereof) immobilised to a solid support according to step (e) of a method according to the present invention and a second source of antigenic molecules consisting essentially of IA-2 antigenic molecules selected from IA-2, one or more variants, analogues, derivatives or fragments thereof with which analyte autoantibodies when present in said sample of body fluid can interact and fusion molecules comprising two or more directly or indirectly fused antigenic molecules selected from IA-2 and one or more variants, analogues, derivatives or fragments thereof, with which analyte autoantibodies when present in said sample of body fluid can interact (such as IA-2, or one or more binding regions thereof, directly or indirectly fused to IA-2 beta, or one or more binding regions thereof), provided with labelling means according to step (f) of a method according to the present invention. A still further alternative according to the present invention may be where a method according to the present invention is required to detect autoantibodies to both GAD and IA-2, where the method comprises providing (i)

first and second sources of GAD antigenic molecules with which analyte autoantibodies when present in said sample of body fluid can interact, and which GAD antigenic molecules are selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$, IA-2, and said one or more variants, analogues, derivatives or fragments thereof and wherein at least one of said antigenic molecules of said fusion molecule comprises $GAD_{65}$, $GAD_{67}$, or one or more variants, analogues, derivatives or fragments thereof, wherein GAD antigenic molecules of said first source are inumobilised to a solid support according to step (e) and GAD antigenic molecules of said second source are provided with labelling means according to step (f); and (ii) first and second sources of IA-2 antigenic molecules with which analyte autoantibodies when present in said sample of body fluid can interact and which IA-2 antigenic molecules are selected from IA-2, one or more variants, analogues, derivatives or fragments thereof, and fusion molecules comprising two or more directly or indirectly fused antigenic molecules selected from IA-2, $GAD_{65}$, $GAD_{67}$ and said one or more variants, analogues, derivatives or fragments thereof and wherein at least one of said antigenic molecules of said fusion molecule comprises IA-2 or one or more variants, analogues, derivatives or fragments thereof, wherein IA-2 antigenic molecules of said first source are immobilised to a solid support according to step (e) and IA-2 antigenic molecules of said second source are provided with labelling means according to step (f).

Accordingly, a preferred embodiment of the present invention may suitably comprise a method of screening a sample of body fluid obtained from an animal subject for analyte autoantibodies reactive with one or more antigenic molecules selected from pancreatic islet cell antigenic molecules, or one or more variants, analogues, derivatives or fragments thereof, said method comprising:
(a) providing said sample of body fluid from said subject;
(b) providing one or more first sources of antigenic molecules with which analyte autoantibodies when present in said sample of body fluid can interact and which antigenic molecules are selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2, and said one or more variants, analogues, derivatives or fragments thereof;
(c) providing one or more second sources of antigenic molecules with which analyte autoantibodies when present in said sample of body fluid can interact and which antigenic molecules are selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof;
(d) contacting said antigenic molecules as provided by steps (b) and (c) simultaneously or successively with said sample of body fluid being screened, whereby analyte autoantibodies when present in said sample of body fluid can interact with said antigenic molecules so as to form one or more complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule;
(e) prior to, or concurrent with, or subsequent to, step (d), providing immobilising means whereby said antigenic molecule of said first source as present in a complex as formed in step (d) is immobilised to a solid support prior to, or concurrent with, or subsequent to, step (d);
(f) prior to, or concurrent with, or subsequent to, step (d), providing direct or indirect detectable labelling means whereby said antigenic molecule of said second source as present in a complex as formed in step (d) is provided with such direct or indirect detectable labelling means prior to, or concurrent with, or subsequent to, step (d); and
(g) detecting the presence of complexes formed in (d) immobilised according to (e) so as to provide an indication of analyte autoantibodies present in said sample.

Alternatively, a preferred embodiment of the present invention may suitably comprise screening a sample of body fluid obtained from an animal subject for analyte autoantibodies reactive only with GAD, or one or more variants, analogues, derivatives or fragments thereof, said method comprising:
(a) providing said sample of body fluid from said subject;
(b) providing first and second sources of antigenic molecules consisting essentially of GAD antigenic molecules selected from $GAD_{65}$, $GAD_{67}$, one or more variants, analogues, derivatives or fragments thereof with which analyte autoantibodies when present in said sample of body fluid can interact and fusion molecules comprising two or more directly or indirectly fused antigenic molecules selected from $GAD_{65}$, $GAD_{67}$ and said one or more variants, analogues, derivatives or fragments thereof, wherein GAD antigenic molecules of said first source are immobilised to a solid support according to step (d) and GAD antigenic molecules of said second source are provided with labelling means according to step (e);
(c) contacting said antigenic molecules as provided by step (b) simultaneously or successively with said sample of body fluid being screened, whereby analyte autoantibodies when present in said sample of body fluid can interact with said antigenic molecules so as to form one or more complexes comprising [GAD antigenic molecule of said first source]-[analyte autoantibody]-[GAD antigenic molecule of said second source];
(d) prior to, or concurrent with, or subsequent to, step (c), providing immobilising means whereby said GAD antigenic molecule of said first source as present in a complex as formed in step (c) is immobilised to a solid support prior to, or concurrent with, or subsequent to, step (c);
(e) prior to, or concurrent with, or subsequent to, step (c), providing direct or indirect detectable labelling means whereby said GAD antigenic molecule of said second source as present in a complex as formed in step (c) is provided with such direct or indirect detectable labelling means prior to, or concurrent with, or subsequent to, step (c); and
(f) detecting the presence of complexes formed in (c) immobilised according to (d) so as to provide an indication of analyte autoantibodies present in said sample.

Alternatively, a preferred embodiment of the present invention may suitably comprise screening a sample of body fluid obtained from an animal subject for analyte autoantibodies reactive with IA-2, or one or more variants, analogues, derivatives or fragments thereof, said method comprising:
   (a) providing said sample of body fluid from said subject;
   (b) providing first and second sources of antigenic molecules consisting essentially of IA-2 antigenic molecules selected from IA-2, one or more variants, analogues, derivatives or fragments thereof with which analyte autoantibodies when present in said sample of body fluid can interact and fusion molecules comprising two or more directly or indirectly fused antigenic molecules selected from IA-2 and said one or more variants, analogues, derivatives or fragments thereof, wherein IA-2 antigenic molecules of said first source are immobilised to a solid support according to step (d) and IA-2 antigenic molecules of said second source are provided with labelling means according to step (e);
   (c) contacting said IA-2 antigenic molecules as provided by step (b) simultaneously or successively with said sample of body fluid being screened, whereby analyte autoantibodies when present in said sample of body fluid can interact with said IA-2 antigenic molecules so as to form one or more complexes comprising [IA-2 antigenic molecule of said first source]-[analyte autoantibody]-[IA-2 antigenic molecule of said second source];
   (d) prior to, or concurrent with, or subsequent to, step (c), providing immobilising means whereby said IA-2 antigenic molecule of said first source as present in a complex as formed in step (c) is immobilised to a solid support prior to, or concurrent with, or subsequent to, step (c);
   (e) prior to, or concurrent with, or subsequent to, step (c), providing direct or indirect detectable labelling means whereby said IA-2 antigenic molecule of said second source as present in a complex as formed in step (c) is provided with such direct or indirect detectable labelling means prior to, or concurrent with, or subsequent to, step (c); and
   (f) detecting the presence of complexes formed in (c) immobilised according to (d) so as to provide an indication of analyte autoantibodies present in said sample.

Alternatively, a preferred embodiment of the present invention may suitably comprise screening a sample of body fluid obtained from an animal subject for first and second analyte autoantibodies respectively reactive with GAD and IA-2, or one or more variants, analogues, derivatives or fragments thereof, said method comprising:
   (a) providing said sample of body fluid from said subject;
   (b) providing first and second sources of GAD antigenic molecules with which analyte autoantibodies when present in said sample of body fluid can interact, and which GAD antigenic molecules are selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$, IA-2, and said one or more variants, analogues, derivatives or fragments thereof and wherein at least one of said antigenic molecules of said fusion molecule comprises $GAD_{65}$, $GAD_{67}$, or one or more variants, analogues, derivatives or fragments thereof, wherein GAD antigenic molecules of said first source are immobilised to a solid support according to step (e) and GAD antigenic molecules of said second source are provided with labelling means according to step (f);
   (c) providing first and second sources of IA-2 antigenic molecules with which analyte autoantibodies when present in said sample of body fluid can interact and which IA-2 antigenic molecules are selected from IA-2, one or more variants, analogues, derivatives or fragments thereof, and fusion molecules comprising two or more directly or indirectly fused antigenic molecules selected from IA-2, $GAD_{65}$, $GAD_{67}$ and said one or more variants, analogues, derivatives or fragments thereof and wherein at least one of said antigenic molecules of said fusion molecule comprises IA-2 or one or more variants, analogues, derivatives or fragments thereof, wherein IA-2 antigenic molecules of said first source are immobilised to a solid support according to step (e) and IA-2 antigenic molecules of said second source are provided with labelling means according to step (f);
   (d) contacting said antigenic molecules as provided by steps (b) and (c) simultaneously or successively with said sample of body fluid being screened, whereby analyte autoantibodies when present in said sample of body fluid can interact with said antigenic molecules so as to form one or more complexes comprising [GAD antigenic molecule of said first source]-[analyte autoantibody]-[GAD antigenic molecule of said second source] or [IA-2 antigenic molecule of said first source]-[analyte autoantibody]-[IA-2 antigenic molecule of said second source];
   (e) prior to, or concurrent with, or subsequent to, step (d), providing immobilising means whereby said GAD or IA-2 antigenic molecule of said first source as present in a complex as formed in step (d) is immobilised to a solid support prior to, or concurrent with, or subsequent to, step (d);
   (f) prior to, or concurrent with, or subsequent to, step (d), providing direct or indirect detectable labelling means whereby said GAD or IA-2 antigenic molecule of said second source as present in a complex as formed in step (d) is provided with such direct or indirect detectable labelling means prior to, or concurrent with, or subsequent to, step (d); and
   (g) detecting the presence of complexes formed in (d) immobilised according to (e) so as to provide an indication of analyte autoantibodies present in said sample.

It may be preferred in a method according to the present invention that the antigenic molecules of the first and second sources when present in said one or more complexes substantially as hereinbefore described both comprise one or more common antigenic molecules. For example, antigenic molecules of said first and second sources when present in the one or more complexes can comprise $GAD_{65}$ or $GAD_{67}$; alternatively the antigenic molecules of the first and second sources when present in the one or more complexes can comprise IA-2.

Alternatively, it may be preferred that one antigenic molecule, of either the first or second source, when present in the one or more complexes comprises an antigenic molecule selected from pancreatic islet cell antigenic molecules and insulin, and the other antigenic molecule when present in the one or more complexes comprises one or more variants, analogues, derivatives or fragments of the above mentioned one antigenic molecule with which analyte autoantibodies when present in said sample of body fluid can interact. For example, where one of the antigenic molecules of the first or second source when present in the one or more complexes comprises $GAD_{65}$ or $GAD_{67}$, the other antigenic molecule when present in the one or more complexes can comprise one or more variants, analogues, derivatives or fragments of $GAD_{65}$ or $GAD_{67}$ with which analyte autoantibodies when present in said sample of body fluid can interact. A further example may be where one of the antigenic molecules of the first or second source when present in the one or more complexes comprises IA-2, and the other antigenic molecule when present in the one or more complexes can comprise one or more variants, analogues, derivatives or fragments of IA-2 with which analyte autoantibodies when present in said sample of body fluid can interact.

A still further alternative embodiment of the present invention may be where both antigenic molecules of the first and second sources when present in the one or more complexes comprise a variant, analogue, derivative or fragment, which may be the same or different, of a common antigenic molecule, with which analyte autoantibodies when present in said sample of body fluid can interact. For example, both antigenic molecules of the first and second sources when present in the one or more complexes can comprise a variant, analogue, derivative or fragment, which may be the same or different, of $GAD_{65}$ or $GAD_{67}$, with which analyte autoantibodies when present in said sample of body fluid can interact. A further example may be where both antigenic molecules of the first and second sources when present in said one or more complexes comprise a variant, analogue, derivative or fragment, which may be the same or different, of IA-2, with which analyte autoantibodies when present in said sample of body fluid can interact. It will be appreciated from the above that where both antigenic molecules when present in the complexes formed according to a method of the present invention comprise variants, analogues, derivatives or fragments derived from a common antigenic molecule, such variants, analogues, derivative or fragments may be the same or different (for example variant 1 and variant 2, where variants 1 and 2 may respectively represent different variants of $GAD_{65}$ or $GAD_{67}$, or fragment 1 and fragment 2, where fragments 1 and 2 may respectively represent different fragments of $GAD_{65}$ or $GAD_{67}$, such as distinct, or possibly overlapping, epitopes of $GAD_{65}$ or $GAD_{67}$).

In the case where fusion molecules are employed in a method according to the present invention, it will be appreciated that such fusion molecules can comprise distinct antigenic molecules (for example $GAD_{65}$ and IA-2) but that in a complex formed according to the present invention the binding regions of antigenic fusion molecules for an analyte autoantibody as respectively provided by the first and second sources will be present in, or will be derived from, a common antigenic molecule. Examples of complexes that may be formed employing one or more fusion molecules according to the present invention can include (i) [GAD-IA-$2_{imm}$]-[analyte autoantibody]-[GAD-IA-$2_{label}$] where in the case where the autoantibody comprises a GAD autoantibody this autoantibody interacts with binding regions of GAD present in [GAD-IA-$2_{imm}$] and [GAD-IA-$2_{label}$], or where the autoantibody comprises a IA-2 autoantibody this autoantibody interacts with binding regions of IA-2 present in [GAD-IA-$2_{imm}$] and [GAD-IA-$2_{label}$], or (ii) [GAD(fragment)$_{imm}$]-[analyte autoantibody]-[GAD-IA-$2_{label}$] where a GAD analyte autoantibody interacts with binding regions of GAD present in [GAD(fragment)$_{imm}$] and [GAD-IA-$2_{label}$], or (iii) [IA-2(fragment)$_{imm}$]-[analyte autoantibody]-[GAD-IA-$2_{label}$] where a IA-2 analyte autoantibody interacts with binding regions of IA-2 present in [IA-2(fragment)$_{imm}$] and [GAD-IA-$2_{label}$], where GAD can represent $GAD_{65}$ or $GAD_{67}$.

Suitably the detectable labelling means can be selected from the group consisting of enzymic labels, isotopic labels, chemiluminescent labels, fluorescent labels, dyes and the like and typically can be selected from the group consisting of alkaline phosphatase, horseradish peroxidase, biotin or the like and in particular can comprise biotin. The monitoring can typically involve reaction of such detectable labelling means (when attached to the one or more antigenic molecules substantially as hereinbefore described, or one or more variants, analogues, derivatives or fragments thereof, or one or more fusion molecules thereof) with one or more substrates therefor (such as an avidin or streptavidin conjugate, for example, streptavidin horseradish peroxidase conjugate or the like), whereby the resulting conjugates can be detected suitably by measurement of optical density or the like.

The detectable labelling means may be directly provided to the one or more antigenic molecules, or one or more one or more variants, analogues, derivatives or fragments thereof or one or more fusion molecules thereof substantially as hereinbefore described. Additionally or alternatively the detectable labelling means may be indirectly provided to the one or more antigenic molecules, or one more one or more variants, analogues, derivatives or fragments thereof, or one or more fusion molecules thereof, substantially as hereinbefore described, typically by providing the detectable labelling means to one or more antibodies or other binding agents which can bind with the one or more antigenic molecules, or one or more variants, analogues, derivatives or fragments thereof, or one or more fusion molecules thereof, substantially as hereinbefore described.

A method of screening for autoantibodies according to the present invention typically comprises directly monitoring interaction of (i) such autoantibodies present in the sample of body fluid from the subject and (ii) one or more antigenic molecules, or one or more variants, analogues, derivatives or fragments thereof, or one or more fusion molecules thereof, substantially as hereinbefore described, as provided by the present invention, typically by employing non-competitive sandwich type assay techniques known in the art.

According to a preferred embodiment of the present invention antigenic molecules of one or more first sources, or one or more variants, analogues, derivatives or fragments thereof, or one or more fusion molecules thereof, substantially as hereinbefore described, are immobilised to a solid support and antigenic molecules of one or more second sources, or one or more variants, analogues, derivatives or fragments thereof, or one or more fusion molecules thereof, substantially as hereinbefore described, are provided with detectable labelling means, and wherein preferably the antigenic molecules of the one or more second sources are provided in solution phase as is conventional for use in known ELISA techniques.

Preferably, in a method according to the present invention, antigenic molecules, or one or more variants, analogues, derivatives or fragments thereof, or one or more fusion molecules thereof, with which analyte autoantibodies when present in said sample of body fluid can interact, of one or more first sources are immobilised to a solid support prior to contact with a sample of body fluid being screened. Such immobilised antigenic molecules of the one or more first sources, or more one or more variants, analogues, derivatives or fragments thereof, or one or more fusion molecules thereof, with which analyte autoantibodies when present in said sample of body fluid can interact, are subsequently contacted with the sample of body fluid being screened either simultaneously or successively with contact of the sample of body fluid with antigenic molecules of one or more second sources, or one or more variants, analogues, derivatives or fragments thereof, or one or more fusion molecules thereof, with which analyte autoantibodies when present in said sample of body fluid can interact. Particularly preferably, immobilised antigenic molecules of the one or more first sources, or one or more variants, analogues, derivatives or fragments thereof, or one or more fusion molecules thereof, with which analyte autoantibodies when present in said sample of body fluid can interact, are contacted with the sample of body fluid being screened so as to form an intermediate complex comprising [antigenic molecule]-[analyte autoantibody] where the antigenic molecule is immobilised to a solid support and the thus formed immobilised intermediate complex is subsequently contacted with antigenic molecules of the one or more second sources, or one or more variants, analogues, derivatives or fragments thereof, or one or more fusion molecules thereof, with which analyte autoantibodies when present in said sample of body fluid can interact, present in solution phase, so as to form the hitherto described complexes comprising [antigenic molecule of said first source]-[analyte autoantibody]-[antigenic molecule of said second source] immobilised to a solid support via the antigenic molecule of the first source.

Accordingly, the present invention provides a method of screening a sample of body fluid obtained from an animal subject for analyte autoantibodies reactive with one or more antigenic molecules selected from pancreatic islet cell antigenic molecules and insulin, or one or more variants, analogues, derivatives or fragments thereof, said method comprising:

(a) providing said sample of body fluid from said subject;
(b) providing one or more first sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof, which antigenic molecules of said one or more first sources are immobilised to a solid support;
(c) providing one or more second sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof, which antigenic molecules of said one or more second sources are provided in solution phase;
(d) contacting said antigenic molecules as provided by steps (b) and (c) simultaneously or successively with said sample of body fluid being screened, whereby analyte autoantibodies when present in said sample of body fluid can interact with said antigenic molecules so as to form one or more immobilised complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule and wherein said complexes are immobilised to a solid support via said antigenic molecule of said first source;
(e) prior to, or concurrent with, or subsequent to, step (d), providing direct or indirect detectable labelling means whereby said antigenic molecule of said second source as present in a complex as formed in step (d) is provided with such direct or indirect detectable labelling means prior to, or concurrent with, or subsequent to, step (d); and
(f) detecting the presence of complexes formed in (d) so as to provide an indication of analyte autoantibodies present in said sample.

The one or more antigenic molecules, or one or more variants, analogues, derivatives or fragments thereof, or fusion molecules thereof, that can react with analyte autoantibodies as required by the present invention can be selected from any pancreatic islet cell antigenic molecule and insulin, and one or more variants, analogues, derivatives or fragments thereof, or fusion molecules thereof and in particular can suitably be selected from the group consisting of glutamic acid decarboxylase (GAD, and in particular the 65 KDa and 67 KDa isoforms of glutamic acid decarboxylase, $GAD_{65}$ and $GAD_{67}$), protein tyrosine phosphatase-like islet cell antigen (IA-2) and insulin, or one or more variants (such as, for example, IA-2 beta), analogues, derivatives or fragments thereof, or fusion molecules comprising two or more of the above, with which analyte autoantibodies when present in said sample of is body fluid can interact. In particular the one or more antigenic molecules, or one or more variants, analogues, derivatives or fragments thereof, that can react with such analyte autoantibodies as required by the present invention, can suitably be selected from the group consisting of glutamic acid decarboxylase (GAD, in particular $GAD_{65}$ or $GAD_{67}$) and protein tyrosine phosphatase-like islet cell antigen (IA-2), or one or more variants, analogues, derivatives or fragments thereof, with which analyte autoantibodies when present in said sample of body fluid can interact.

Other contacting techniques are, however, possible, for example it is possible according to the present invention not to initially immobilise the antigenic molecules, or one or more variants, analogues, derivatives or fragments thereof, or one or more fusion molecules thereof, of the one or more first antigen sources, prior to a contacting step as described above, but to initially contact the solid support substantially as hereinbefore described with a binder for the antigenic molecules, or one or more variants, analogues, derivatives or fragments thereof, or one or more fusion molecules thereof; of the one or more first antigen sources and to subsequently contact the so treated solid support with the above described antigenic molecules of the one or more first and second sources, or one or more variants, analogues, derivatives or fragments thereof; or one or more fusion molecules thereof, and the sample of body fluid being screened.

In respect of the solid supports and conditions employed in the present invention, the supports and conditions do not generally fundamentally differ from conventional supports and conditions employed in known immunoassay techniques. A solid support for use according to the present invention can comprise an ELISA plate as currently employed in known ELISA techniques, or may employ any other suitable support for use in the present invention, such as tubes, particles, magnetic beads, nitrocellulose or the like.

There is also provided by the present invention a kit for screening a sample of body fluid obtained from an animal subject for analyte autoantibodies reactive with one or more antigenic molecules selected from pancreatic islet cell antigenic molecules and insulin, or one or more variants, analogues, derivatives or fragments thereof, said kit comprising:

(a) one or more first sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof;

(b) one or more second sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof;

(c) means for contacting said antigenic molecules as provided by (a) and (b) simultaneously or successively with said sample of body fluid being screened, whereby analyte autoantibodies when present in said sample of body fluid can interact with said antigenic molecules so as to form one or more complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule;

(d) means for immobilising to a solid support, said antigenic molecule of said first source as present in a complex as defined in (c), prior to, or concurrent with, or subsequent to, contact of the antigenic molecule of said first source with the sample of body fluid being screened;

(e) means for providing direct or indirect detectable labelling means to said antigenic molecule of said second source as present in a complex as defined in (c), prior to, or concurrent with, or subsequent to, contact of said antigenic molecule of said second source with said sample of body fluid being screened; and (f) means for detecting the presence of complexes as defined in (c) immobilised as defined in (d) so as to provide an indication of analyte autoantibodies present in said sample.

A kit for screening for analyte autoantibodies according to the present invention is particularly advantageous in enabling such autoantibody detection of high specificity and sensitivity.

The one or more antigenic molecules, or one or more variants, analogues, derivatives or fragments thereof, or fusion molecules thereof, that can react with analyte autoantibodies as required by the present invention can be selected from any pancreatic islet cell antigenic molecule and insulin, and one or more variants, analogues, derivatives or fragments thereof, or fusion molecules thereof and in particular can suitably be selected from the group consisting of glutamic acid decarboxylase (GAD, and in particular the 65 KDa and 67 KDa isoforms of glutamic acid decarboxylase, $GAD_{65}$ and $GAD_{67}$), protein tyrosine phosphatase-like islet cell antigen (IA-2) and insulin, or one or more variants (such as, for example, IA-2 beta), analogues, derivatives or fragments thereof, or fusion molecules comprising two or more of the above, with which analyte autoantibodies when present in said sample of body fluid can interact. In particular the one or more antigenic molecules, or one or more variants, analogues, derivatives or fragments thereof, that can react with such analyte autoantibodies as required by the present invention, can suitably be selected from the group consisting of glutamic acid decarboxylase (GAD, in particular $GAD_{65}$ or $GAD_{67}$) and protein tyrosine phosphatase-like islet cell antigen (IA-2), or one or more variants, analogues, derivatives or fragments thereof, with which analyte autoantibodies when present in said sample of body fluid can interact. Various embodiments of the antigenic molecules and suitable fusion molecules for use in a kit according to the present invention are substantially as hereinbefore described in greater detail with reference to a method according to the present invention.

In a preferred aspect of the present invention, therefore, a kit for screening substantially as hereinbefore described is for use in detecting analyte autoantibodies to $GAD_{65}$ or $GAD_{67}$ and/or IA-2, or one or more variants, analogues, derivatives or fragments thereof, and the one or more antigenic molecules comprise $GAD_{65}$ or $GAD_{67}$, or one or more variants, analogues, derivatives or fragments thereof, and/or IA-2, or one or more variants, analogues, derivatives or fragments thereof. In the case where fusion antigenic molecules are employed in a kit according to the present invention, suitable fusion molecules may comprise two or more directly or indirectly fused antigenic molecules selected from $GAD_{65}$, $GAD_{67}$, IA-2 and said one or more variants, analogues, derivatives or fragments thereof substantially as hereinbefore described in greater detail with reference to a method according to the present invention.

Preferably a kit according to the present invention comprises one or more first sources of antigenic molecules selected from $GAD_{65}$, $GAD_{67}$, IA-2, insulin, one or more variants, analogues, derivatives or fragments thereof, and fusion molecules comprising two or more directly or indirectly fused antigenic molecules selected from $GAD_{65}$, $GAD_{67}$, IA-2, insulin and said one or more variants, analogues, derivatives or fragments thereof, with which analyte autoantibodies when present in said sample of body fluid can interact, immobilised to a solid support as defined in (d) and one or more second sources of antigenic molecules selected from $GAD_{65}$, $GAD_{67}$, IA-2, insulin, one or more variants, analogues, derivatives or fragments thereof, and fusion molecules comprising two or more directly or indirectly fused antigenic molecules selected from $GAD_{65}$, $GAD_{67}$, IA-2, insulin and one or more variants, analogues, derivatives or fragments thereof, with which analyte autoantibodies when present in said sample of body fluid can interact, provided with labelling means as defined in (e).

More preferably, a kit according to the present invention comprises one or more first sources of antigenic molecules selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof, with which analyte autoantibodies when present in said sample of body fluid can interact, immobilised to a solid support as defined in (d) and one or more second sources of antigenic molecules selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof, with which analyte autoantibodies when present in said sample of body fluid can interact, provided with labelling means as defined in (e): It may be preferred that a kit according to the present invention comprises a first source of antigenic molecules consisting essentially of GAD antigenic molecules selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$ and said one or more variants, analogues, derivatives or fragments thereof with which analyte autoantibodies when present in said sample of body fluid can interact, inumobilised to a solid support as defined in (d), and a second source of antigenic molecules consisting essentially of GAD antigenic molecules selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$ and said one or more variants, analogues, derivatives or fragments thereof, with which analyte autoantibodies when present in said sample of body fluid can interact, provided with labelling means as defined in (e). Alternatively, it may be preferred that a kit according to the present invention comprises a first source of antigenic molecules consisting essentially of IA-2 antigenic molecules selected from IA-2, one or more variants, analogues, derivatives or fragments thereof, with which analyte autoantibodies when present in said sample of body fluid can interact and fusion molecules comprising two or more directly or indirectly fused antigenic molecules selected from IA-2 and said one or more variants, analogues, derivatives or fragments thereof, immobilised to a solid support as defined in (d), and a second source of antigenic molecules consisting essentially of IA-2 antigenic molecules selected from IA-2, one or more variants, analogues, derivatives or fragments thereof, with which analyte autoantibodies when present in said sample of body fluid can interact and fusion molecules comprising two or more directly or indirectly fused antigenic molecules selected from IA-2 and said one or more variants, analogues, derivatives or fragments thereof, provided with labelling means as defined in (e). A still further alternative according to the present invention may be where a kit according to the present invention comprises (i) first and second sources of GAD antigenic molecules with which analyte autoantibodies when present in said sample of body fluid can interact, and which GAD antigenic molecules are selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof and wherein at least one of said antigenic molecules of said fusion molecule comprises $GAD_{65}$, $GAD_{67}$, or one or more variants, analogues, derivatives or fragments thereof, wherein GAD antigenic molecules of said first source are immobilised to a solid support as defined in (d) and GAD antigenic molecules of said second source are provided with labelling means as defined in (e); and (ii) first and second sources of IA-2 antigenic molecules with which analyte autoantibodies when present in said sample of body fluid can interact and which IA-2 antigenic molecules are selected from IA-2, one or more variants, analogues, derivatives or fragments thereof, and fusion molecules comprising two or more directly or indirectly fused antigenic molecules selected from IA-2, $GAD_{65}$, $GAD_{67}$ and said one or more variants, analogues, derivatives or fragments thereof and wherein at least one of said antigenic molecules of said fusion molecule comprises IA-2 or one or more variants, analogues, derivatives or fragments thereof, wherein IA-2 antigenic molecules of said first source are immobilised to a solid support according as defined in (d) and IA-2 antigenic molecules of said second source are provided with labelling means as defined in (e).

Accordingly, a preferred embodiment of the present invention may suitably comprise a kit for screening a sample of body fluid obtained from an animal subject for analyte autoantibodies reactive with one or more antigenic molecules selected from pancreatic islet cell antigenic molecules, or one or more variants, analogues, derivatives or fragments thereof, said kit comprising:

(a) one or more first sources of antigenic molecules with which analyte autoantibodies when present in said sample of body fluid can interact and which antigenic molecules are selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof, (b) one or more second sources of antigenic molecules with which analyte autoantibodies when present in said sample of body fluid can interact and which antigenic molecules are selected from $GAD_{65}$, $GAD_{67}$, IA-2, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof;

(c) means for contacting said antigenic molecules as provided by (a) and (b) simultaneously or successively with said sample of body fluid being screened, whereby analyte autoantibodies when present in said sample of body fluid can interact with said antigenic molecules so as to form one or more complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule;

(d) means for immobilising to a solid support said antigenic molecule of said first source as present in a complex as defined in (c), prior to, or concurrent with, or subsequent to, contact of said antigenic molecule of said first source with the sample of body fluid being screened;

(e) means for providing direct or indirect detectable labelling means to said antigenic molecule of said second source as present in a complex as defined in (c), prior to, or concurrent with, or subsequent to, contact of said antigenic molecule of said second source with the sample of body fluid being screened; and (f) means for detecting the presence of complexes as defined in (c) immobilised as defined in (d) so as to provide an indication of analyte autoantibodies present in said sample.

Alternatively, a preferred embodiment of the present invention may suitably comprise a kit for screening a sample of body fluid obtained from an animal subject for analyte autoantibodies reactive with GAD, or one or more variants, analogues, derivatives or fragments thereof, said kit comprising:

(a) first and second sources of antigenic molecules consisting essentially of GAD antigenic molecules selected from $GAD_{65}$, $GAD_{67}$, one or more variants, analogues, derivatives or fragments thereof with which analyte autoantibodies when present in said sample of body fluid can interact and fusion molecules comprising two or more directly or indirectly fused antigenic molecules selected from $GAD_{65}$, $GAD_{67}$ and said one or more variants, analogues, derivatives or fragments thereof, wherein GAD antigenic molecules of said first source are immobilised to a solid support as defined in (c) and GAD antigenic molecules of said second source are provided with labelling means as defined in (d);

(b) means for contacting said antigenic molecules as provided by (a) simultaneously or successively with said sample of body fluid being screened, whereby analyte autoantibodies when present in said sample of body fluid can interact with said antigenic molecules so as to form one or more complexes comprising [GAD antigenic molecule of said first source]-[analyte autoantibody]-[GAD antigenic molecule of said second source];

(c) means for immobilising to a solid support said GAD antigenic molecule of said first source as present in a complex as defined in (b), prior to, or concurrent with, or subsequent to, contact of said GAD antigenic molecule of said first source with the sample of body fluid being screened;

(d) means for providing direct or indirect detectable labelling means to said GAD antigenic molecule of said second source as present in a complex as defined in (b), prior to, or concurrent with, or subsequent to, contact of said GAD antigenic molecule of said second source with the sample of body fluid being screened; and (e) means for detecting the presence of complexes as defined in (b) immobilised as defined in (c) so as to provide an indication of analyte autoantibodies present in said sample.

Alternatively, a preferred embodiment of the present invention may suitably comprise a kit for screening a sample of body fluid obtained from an animal subject for analyte autoantibodies reactive with IA-2, or one or more variants, analogues, derivatives or fragments thereof, said kit comprising:

(a) first and second sources of antigenic molecules consisting essentially of IA-2 antigenic molecules selected from IA-2, one or more variants, analogues, derivatives or fragments thereof, with which analyte autoantibodies when present in said sample of body fluid can interact and fusion molecules comprising two or more directly or indirectly fused antigenic molecules selected from IA-2 and said one or more variants, analogues, derivatives or fragments thereof, wherein IA-2 antigenic molecules of said first source are immobilised to a solid support as defined in (c) and IA-2 antigenic molecules of said second source are provided with labelling means as defined in (d);

(b) means for contacting said IA-2 antigenic molecules as provided by (a) simultaneously or successively with said sample of body fluid being screened, whereby analyte autoantibodies when present in said sample of body fluid can interact with said IA-2 antigenic molecules so as to form one or more complexes comprising [IA-2 antigenic molecule of said first source]-[analyte autoantibody]-[IA-2 antigenic molecule of said second source];

(c) means for immobilising to a solid support said IA-2 antigenic molecule of said first source as present in a complex as defined in (b), prior to, or concurrent with, or subsequent to, contact of said IA-2 antigenic molecule of said first source with the sample of body fluid being screened;

(d) means for providing direct or indirect detectable labelling means to said IA-2 antigenic molecule of said second source as present in a complex as defined in (b), prior to, or concurrent with, or subsequent to, contact of said IA-2 antigenic molecule of said second source with the sample of body fluid being screened; and (e) means for detecting the presence of complexes as defined in (b) immobilised as defined in (c) so as to provide an indication of analyte autoantibodies present in said sample.

Alternatively, a preferred embodiment of the present invention may suitably comprise a kit for screening a sample of body fluid obtained from an animal subject for first and second analyte autoantibodies respectively reactive with GAD and IA-2, or one or more variants, analogues, derivatives or fragments thereof, said kit comprising:

(a) first and second sources of GAD antigenic molecules with which analyte autoantibodies when present in said sample of body fluid can interact, and which GAD antigenic molecules are selected from $GAD_{65}$, $GAD_{67}$, one or more variants, analogues, derivatives or fragments thereof and fusion molecules comprising two or more directly or indirectly fused antigenic molecules selected from $GAD_{65}$, $GAD_{67}$, IA-2 and said one or more variants, analogues, derivatives or fragments thereof and wherein at least one of said antigenic molecules of said fusion molecule comprises $GAD_{65}$, $GAD_{67}$, or one or more variants, analogues, derivatives or fragments thereof, wherein GAD antigenic molecules of said first source are immobilised to a solid support as defined in (d) and GAD antigenic molecules of said second source are is provided with labelling means as defined in (e);

(b) first and second sources of IA-2 antigenic molecules with which analyte autoantibodies when present in said sample of body fluid can interact and which IA-2 antigenic molecules are selected from IA-2, one or more variants, analogues, derivatives or fragments thereof, and fusion molecules comprising two or more directly or indirectly fused antigenic molecules selected from IA-2, $GAD_{65}$, $GAD_{67}$ and said one or more variants, analogues, derivatives or fragments thereof and wherein at least one of said antigenic molecules of said fusion molecule comprises IA-2 or one or more variants, analogues, derivatives or fragments thereof, wherein IA-2 antigenic molecules of said first source are immobilised to a solid support according as defined in (d) and IA-2 antigenic molecules of said second source are provided with labelling means as defined in (e);

(c) means for contacting said antigenic molecules as provided by (a) and (b) simultaneously or successively with said sample of body fluid being screened, whereby analyte autoantibodies when present in said sample of body fluid can interact with said antigenic molecules so as to form one or more complexes comprising [GAD antigenic molecule of said first source]-[analyte autoantibody]-[GAD antigenic molecule of said second source] or [IA-2 antigenic molecule of said first source]-[analyte autoantibody]-[IA-2 antigenic molecule of said second source];

(d) means for immobilising to a solid support said GAD or IA-2 antigenic molecule of said first source as present in a complex as defined in (c), prior to, or concurrent with, or subsequent to, contact of said GAD or IA-2 antigenic molecule of said first source with the sample of body fluid being screened;

(e) means for providing direct or indirect detectable labelling means to said GAD or IA-2 antigenic molecule of said second source as present in a complex as defined in (c), prior to, or concurrent with, or subsequent to, contact of said GAD or IA-2 antigenic molecule of said second source with the sample of body fluid being screened; and (f) means for detecting the presence of complexes as defined in (c) immobilised as defined in (d) so as to provide an indication of analyte autoantibodies present in said sample.

It may be preferred in a kit according to the present invention that the antigenic molecules of the first and second sources comprise one or more common antigenic molecules. For example, antigenic molecules of said first and second sources may comprise $GAD_{65}$ or $GAD_{67}$; alternatively antigenic molecules of the first and second sources may both comprise IA-2.

Alternatively, it may be preferred that the antigenic molecules, of either the first or second source, are selected from pancreatic islet cell antigenic molecules and insulin, and the antigenic molecules of the other source comprises one or more variants, analogues, derivatives or fragments of the above mentioned antigenic molecules of either the first or second source, with which analyte autoantibodies when present in said sample of body fluid can interact. For example, where the antigenic molecules of either the first or second source comprise $GAD_{65}$ or $GAD_{67}$, the antigenic molecules of the other source comprise one or more variants, analogues, derivatives or fragments of $GAD_{65}$ or $GAD_{67}$ with which analyte autoantibodies when present in said sample of body fluid can interact. A further example may be where the antigenic molecules of either the first or second source comprise IA-2, and the antigenic molecules of the other source comprise one or more variants, analogues, derivatives or fragments of IA-2 with which analyte autoantibodies when present in said sample of body fluid can interact.

A still further alternative embodiment of the present invention may be where both antigenic molecules of the first and second sources comprise a variant, analogue, derivative or fragment, which may be the same or different, of a common antigenic molecule, with which analyte autoantibodies when present in said sample of body fluid can interact. For example, antigenic molecules of both the first and second sources can comprise a variant, analogue, derivative or fragment, which may be the same or different, of $GAD_{65}$ or $GAD_{67}$, with which analyte autoantibodies when present in said sample of body fluid can interact. A further example may be where antigenic molecules of both the first and second sources comprise a variant, analogue, derivative or fragment, which may be the same or different, of IA-2, with which analyte autoantibodies when present in said sample of body fluid can interact. It will be appreciated from the above that where antigenic molecules of the first and second sources comprise variants, analogues, derivatives or fragments derived from a common antigenic molecule, such variants, analogues, derivative or fragments as provided by the respective sources, may be the same or different (for example variant 1 provided by the first source of antigenic molecules and variant 2 provided by the second source of antigenic molecules, where variants 1 and 2 may respectively represent different variants of $GAD_{65}$ or $GAD_{67}$, or fragment 1 provided by the first source of antigenic molecules and fragment 2 provided by the second source of antigenic molecules, where fragments 1 and 2 may respectively represent different fragments of $GAD_{65}$ or $GAD_{67}$, such as distinct, or possibly overlapping, epitopes of $GAD_{65}$ or $GAD_{67}$).

Suitably the detectable labelling means can be selected from the group consisting of enzymic labels, isotopic labels, chemiluminescent labels, fluorescent labels, dyes and the like and typically can be selected from the group consisting of alkaline phosphatase, horseradish peroxidase, biotin-or the like and in particular can comprise biotin. Suitably such detectable labelling means (when attached to the one or more antigenic molecules substantially as hereinbefore described, or one or more variants, analogues, derivatives or fragments thereof, or one or more fusion molecules thereof) can be reacted with one or more substrates therefor (such as an avidin or streptavidin conjugate, for example, streptavidin horseradish peroxidase conjugate or the like), whereby the resulting conjugates can be detected suitably by measurement of optical density or the like.

The detectable labelling means may be directly provided to the one or more antigenic molecules, or one or more one or more variants, analogues, derivatives or fragments thereof, or one or more fusion molecules thereof, substantially as hereinbefore described. Additionally or alternatively the detectable labelling means may be indirectly provided to the one or more antigenic molecules, or one or more variants, analogues, derivatives or fragments thereof, or one or more fusion molecules thereof, substantially as hereinbefore described, typically by providing the detectable labelling means to one or more antibodies or other binding agents which can bind with the one or more antigenic molecules, or one or more variants, analogues, derivatives or fragments thereof or one or more fusion molecules thereof, substantially as hereinbefore described.

A kit for screening for autoantibodies according to the present invention typically further comprises means for directly monitoring interaction of (i) such autoantibodies present in the sample of body fluid from the subject and (ii) one or more antigenic molecules, or one or more variants, analogues, derivatives or fragments thereof, or one or more fusion molecules thereof, substantially as hereinbefore described, as provided by the present invention, typically by employing non-competitive sandwich type assay techniques known in the art.

According to a preferred embodiment of the present invention antigenic molecules of one or more first sources, or one or more variants, analogues, derivatives or fragments thereof, or one or more fusion molecules thereof, substantially as hereinbefore described, are immobilised to a solid support and antigenic molecules of one or more second sources, or one or more variants, analogues, derivatives or fragments thereof, or one or more fusion molecules thereof, substantially as hereinbefore described, are provided with detectable labelling means, and wherein preferably the antigenic molecules of the one or more second sources are provided in solution phase as is conventional for use in known ELISA techniques.

Preferably, a kit according to the present invention comprises immobilising means whereby antigenic molecules, or one or more variants, analogues, derivatives or fragments thereof, or one or more fusion molecules thereof, with which analyte autoantibodies when present in said sample of body fluid can interact, of one or more first sources are immobilised to a solid support prior to contact with a sample of body fluid being screened. Suitably a kit according to the present invention comprises contacting means whereby such immobilised antigenic molecules of the one or more first sources, or one or more variants, analogues, derivatives or fragments thereof, or one or more fusion molecules thereof, with which analyte autoantibodies when present in said sample of body fluid can interact, can be contacted with the sample of body fluid being screened either simultaneously or successively with contact of the sample of body fluid with antigenic molecules of one or more second sources, or more one or more variants, analogues, derivatives or fragments thereof or one or more fusion molecules thereof, with which analyte autoantibodies when present in said sample of body fluid can interact. Particularly preferably, contacting means are provided whereby immobilised antigenic molecules of the one or more first sources, or one or more variants, analogues, derivatives or fragments thereof, or one or more fusion molecules thereof, with which analyte autoantibodies when present in said sample of body fluid can interact, are contacted with the sample of body fluid being screened so as to form an intermediate complex comprising [antigenic molecule]-[analyte autoantibody] where the antigenic molecule is immobilised to a solid support and the thus formed immobilised intermediate complex is subsequently contacted with molecules of the one or more second sources, or one or more variants, analogues, derivatives or fragments thereof, or one or more fusion molecules thereof, with which analyte autoantibodies when present in said sample of body fluid can interact, present in solution phase, so as to form the hitherto described complex comprising [antigenic molecule of said first source]-[analyte autoantibody]-[antigenic molecule of said second source] immobilised to a solid support via the antigenic molecule of said first source.

Accordingly, the present invention provides a kit for screening a sample of body fluid obtained from an animal subject for analyte autoantibodies reactive with one or more antigenic molecules selected from pancreatic islet cell antigenic molecules and insulin, or one or more variants, analogues, derivatives or fragments thereof, said kit comprising:

(a) one or more first sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof, wherein said antigenic molecules of said one or more first sources are immobilised to a solid support;

(b) one or more second sources of antigenic molecules with which analyte autoantibodies when present in said sample of body fluid can interact and which antigenic molecules are selected from pancreatic islet cell antigenic molecules, insulin, one or more variants, analogues, derivatives or fragments of said pancreatic islet cell antigenic molecules or insulin, and fusion molecules comprising two or more directly or indirectly fused antigenic molecules selected from pancreatic islet cell antigenic molecules, insulin and said one or more variants, analogues, derivatives or fragments thereof, which antigenic molecules of said one or more second sources are provided in solution phase and are provided with labelling means as defined in (d);

(c) means for contacting said antigenic molecules as provided by (a) and (b) simultaneously or successively with said sample of body fluid being screened, whereby analyte autoantibodies when present in said sample of body fluid can interact with said antigenic molecules so as to form one or more immobilised complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule, which immobilised complexes are immobilised to a solid support via said antigenic molecule of said first source present in said complex;

(d) means for providing direct or indirect detectable labelling means to said antigenic molecule of said second source as present in a complex as defined in (c), prior to, or concurrent with, or subsequent to, contact of said antigenic molecule of said second source with said sample of body fluid being screened; and (e) means for detecting the presence of complexes as defined in (c) so as to provide an indication of analyte autoantibodies present in said sample.

Other contacting means may, however, be present in a kit according to the present invention, for example it is possible according to the present invention not to provide means for initially immobilising the antigenic molecules, or one or more variants, analogues, derivatives or fragments thereof, or one or more fusion molecules thereof, of the one or more first antigen sources, prior to a contacting step as described above, but to provide means to initially contact the solid support substantially as hereinbefore described with a binder for the antigenic molecules, or one or more variants, analogues, derivatives or fragments thereof, or one or more fusion molecules thereof, of the one or more first antigen sources and for the kit to comprise means for subsequently contacting the so treated solid support with the above described antigenic molecules or the one or more first and second sources, or one or more variants, analogues, derivatives or fragments thereof, or one or more fusion molecules thereof, and the sample of body fluid being screened.

In respect of the solid supports and conditions employed in a kit according to the present invention, the supports and conditions do not generally fundamentally differ from conventional supports and conditions employed in known immunoassay techniques. A solid support for use in a kit according to the present invention can comprise an ELISA plate as currently employed in known ELISA techniques, or may employ any other suitable support for use in the present invention, such as tubes, particles, magnetic beads, nitrocellulose or the like.

Detection of analyte autoantibodies reactive with one or more antigenic molecules selected from pancreatic islet cell antigenic molecules and insulin according to a method provided by the present invention, or employing a kit provided by the present invention, can be useful in the diagnosis of a number of disease states with which the presence of such analyte autoantibodies is associated. In particular, the present invention can be employed in screening a sample of body fluid from an animal subject suspected of suffering from, susceptible to or having any of the following disease states—type 1 diabetes mellitus and/or stiff man syndrome, type 2 diabetes mellitus, one or more autoimmune thyroid diseases, celiac disease, one or more connective tissue diseases, adrenal autoimmunity, or a combination of two or more different autoimmune diseases and the present invention further provides a method of diagnosing any of the above disease states in an animal subject.

It will be appreciated from the foregoing description that the present invention provides assay methods and kits for detecting, in a sample of body fluid obtained from an animal subject, analyte autoantibodies reactive with one or more antigenic molecules selected from pancreatic islet cell antigenic molecules and insulin and indicative of the onset or presence of the above disease states. The detection of such autoantibodies in the sample of body fluid (or at least the level of such autoantibodies in the sample) is indicative of the likely onset or presence of such disease states in the subject from which the sample is obtained and can, therefore, enable the diagnosis of the likely onset or presence of such disease states.

There is, therefore, further provided by the present invention a method of diagnosing the likely onset or presence of disease states, associated with the presence of autoantibodies reactive with one or more antigenic molecules selected from pancreatic islet cell antigenic molecules and insulin, in an animal subject (in particular a human subject); suspected of having or being susceptible to these disease states, the method comprising detecting autoantibodies reactive with one or more antigenic molecules selected from pancreatic islet cell antigenic molecules and insulin, and being indicative of the likely onset or presence of these disease states in a sample of body fluid from the subject substantially as hereinbefore described, and whereby the detected autoantibodies can provide a diagnosis of the likely onset or presence of these disease states.

There is, therefore, still further provided by the present invention a method of delaying or preventing the onset of disease states, associated with the presence of autoantibodies reactive with one or more antigenic molecules selected from pancreatic islet cell antigenic molecules and insulin, in an animal subject (in particular a human subject), or treating an animal subject (in particular a human subject) having or recovering from such disease states, which method comprises initially detecting autoantibodies reactive with one or more antigenic molecules selected from pancreatic islet cell antigenic molecules and insulin, and being indicative of the onset or presence of such disease states, in a sample of body fluid obtained from the subject substantially as hereinbefore described, thereby providing a diagnosis of the likely onset or presence of such disease states in the subject, and administering to the subject a therapeutically effective amount of at least one therapeutic agent effective in delaying onset, obviating, preventing and/or treating these disease states.

There is, therefore, still further provided by the present invention a method of assessing the effectiveness of delaying or preventing the onset of disease states, associated with the presence of autoantibodies reactive with one or more antigenic molecules selected from pancreatic islet cell antigenic molecules and insulin, in an animal subject (in particular a human subject), or assessing the effectiveness of treating an animal subject (in particular a human subject) having or recovering from such disease states, which method comprises administering to the subject a therapeutically effective amount of at least one therapeutic agent effective in delaying onset, obviating, preventing and/or treating such disease states associated with the presence of autoantibodies reactive with one or more antigenic molecules selected from pancreatic islet cell antigenic molecules and insulin, and detecting autoantibodies indicative of the onset or presence of such disease states in a sample of body fluid obtained from the subject, so as to provide an indication of the presence of said autoantibodies in said sample, thereby providing an indication of the effectiveness of treating the subject, or of delaying or preventing the onset of such disease states in the subject.

There is still further provided by the present invention, in combination, a kit substantially as hereinbefore described, together with a therapeutically effective amount of at least one therapeutic agent effective in the treatment of disease states associated with the presence of autoantibodies reactive with one or more antigenic molecules selected from pancreatic islet cell antigenic molecules and insulin.

A sample of body fluid being screened by the present invention will typically comprise blood samples or other fluid blood fractions, such as in particular serum samples or plasma samples, but the sample may in principle be another biological fluid, such as saliva or urine or solubilised tissue extracts.

The term "antigen" or "antigenic molecules" as used herein denotes a compound with which antibodies as described herein can interact and which is capable of binding to an antibody to form specific antibody-antigen complexes. The antigen or antigenic molecules may be natural or synthetic and modifications thereto are preferably such as to not detrimentally affect the binding properties thereof to a specific antibody.

As indicated above, the present invention covers the use of "variants", "analogs", "derivatives" and "fragments" of antigenic molecules as described herein and the terms "variants", "analogs", "derivatives" and "fragments" as used herein can be characterised as polypeptides which retain essentially the same biological function or activity as naturally occurring antigenic molecules and in particular in respect of the binding properties thereof for a specific antibody. Suitably, variants, analogs, derivatives and fragments, and variants, analogs and derivatives of the fragments as described herein, have a primary structural conformation of amino acids in which several or a few (such as 5 to 10, 1 to 5 or 1 to 3) amino acid residues of the naturally occurring antigenic molecules are substituted, deleted or added, in any combination. Especially preferred among these are silent substitutions, additions are deletions which do not alter or substantially alter the biological activity or function of the naturally occurring antigenic molecules. Conservative substitutions can be preferred as hereinafter described in greater detail.

More particularly, variants, analogs or derivatives of antigenic molecules suitable for use according to the present invention may be ones in which one or more of the amino acid residues are substituted with a conserved or non-conserved amino acid residue (preferably a conserved amino acid residue), or ones in which one or more of the amino acid resides includes a substituent group or the like. Such variants, derivatives and analogs are deemed to be within the scope of those skilled in the art from the teachings herein.

Most typically, variants, analogs or derivatives are those that vary from a reference (such as naturally occurring antigenic molecules as referred to herein) by conservative amino acid substitutions. Such substitutions are those that substitute a given amino acid in a polypeptide by another amino acid of like characteristics. Typically seen as conservative substitutions are the replacements, one for another, among the aliphatic amino acids A, V, L and I; among the hydroxyl residues S and T; among the acidic residues D and E; among the amide residues N and Q; among the basic residues K and R; and among the aromatic residues F and Y.

More particularly, the term "fragment" as used herein denotes a polypeptide having an amino acid sequence that entirely is the same as part but not all of the amino acid sequence of naturally occurring amino acids as referred to herein, and variants or derivatives thereof and such fragments may be "free standing", i.e. not part of or fused to other amino acids or polypeptides, or they may be comprised within a larger polypeptide of which they form a part or region. In the context of the present invention, it will be appreciated that particularly preferred fragments for use according to the present invention may be one or more epitopes of antigenic molecules as referred to herein and as described above such epitope fragments may be used in "free standing" form or may be used within a larger polypeptide, such as a scaffold polypeptide, of which they form a part or region. The use of such epitope fragments in substantially isolated or free standing form according to the present invention can be advantageous in terms of enhanced stability of such substantially isolated or free standing epitope fragments when compared with the use of a fun length antigen and/or enhanced specificity associated with the use of such substantially isolated or free stranding epitope fragments compared with the use of a full length antigen.

The present invention will now be further illustrated by the following example, which does not limit the scope of the invention in any way.

EXAMPLE

Preparation of $GAD_{65}$ Coated ELISA Plates

Human recombinant $GAD_{65}$ of >95% purity as assessed by SDS-PAGE (M Powell, L Prentice, T Asawa, R Kato, J Sawicka, H Tanaka, V Petersen, A Munkley, S Morgan, B Rees Smith, J Furmaniak. Clinica Chimica Acta, 1996 256: 175-188) was diluted to 150 µg/L in a coating buffer comprising 1.59 g/L $Na_2CO_3$, 2.94 g/L $NaHCO_3$, 0.1 g/L $NaN_3$, 0.01 g/L Phenol Red, and 5 mg/L BSA (pH 9.2) and 150 µL of the resulting solution was added to 96-well ELISA plates (available under the trade mark Nunc F8 MaxiSorp). The plates were then incubated overnight at 4° C., the contents of the wells aspirated and the wells washed three times with a high salt buffer (HSB) comprising 10 g/L BSA, 1 g/L $NaN_3$, 11.69 g/L NaCl, 18.17 g/L Tris, and 10 mL/L Polyoxyethylene-Sorbitan Monolaurate (available under the trade mark Tween 20 (pH 8.3). A post-coat buffer comprising 3 g/L BSA, 9 g/L NaCl, 20 g/L sucrose and 0.2 g/L $NaN_3$ was added to the wells (250 µL per well) and incubated for 30 minutes at room temperature. The post-coat buffer was then aspirated, the plates dried under vacuum and stored in sealed bags with silica gel at 4° C. until use.

Labelling of $GAD_{65}$ with Biotin

Human recombinant $GAD_{65}$ in PBS (1.15 g/L $Na_2HPO_4$, 0.2 g/L $KH_2PO_4$, 0.2 g/L KCl, 8 g/L NaCl) was reacted with a commercial biotinylation reagent (Sulfo-NHS-LC-LC-Biotin available under the trade mark EZ-Link from Perbio Science), at a molar ratio of 1 part $GAD_{65}$ to 24 parts biotinylation reagent for 30 minutes at room temperature. The reaction was stopped by dialysis against PBS at 4° C. and the resulting material was stored at −70° C. in small aliquots.

The resulting $GAD_{65}$ labelled with biotin according to the above techniques ($GAD_{65}$-Bi) was diluted to 3 mg/L in 20 g/L BSA, filtered through a 0.22 µm filter, aliquotted at 1 mL per vial, freeze dried and then stored at −20° C. To use, 7.5 mL of HSB was added to the vial, giving a final concentration of $GAD_{65}$-Bi of 400 µg/L.

Preparation of Calibrators for $GAD_{65}$ Autoantibody Assay

IgG preparations of three human monoclonal autoantibodies to $GAD_{65}$ (M J Powell, N Hayakawa, M Masuda, J Sanders, M Evans, LDKE Premawardhana, J Furmaniak, B Rees Smith. Isolation and characterization of three human monoclonal antibodies to glutamic acid decarboxylase ($GAD_{65}$) from a patient without clinical diabetes. Diabetes/Metabolism Research and Reviews, 2001 17 (S1): 021) were diluted in HSB to give an absorbance at OD450 nm from 4.0 to 0.1. These monoclonal antibodies are known to be representative of $GAD_{65}$ autoantibodies found in sera from patients with type 1 diabetes (M J Powell, N Hayakawa, M Masuda, J Sanders, M Evans, LDKE Premawardhana, J Furmaniak, B Rees Smith. Isolation and characterization of three human monoclonal antibodies to glutamic acid decarboxylase ($GAD_{65}$) from a patient without clinical diabetes. Diabetes/Metabolism Research and Reviews, 2001 17 (S1): 021).

$GAD_5$ Autoantibody Detection

Plates coated with $GAD_{65}$ prepared according to the above techniques were brought to room temperature and 25 µL of undiluted serum sample obtained from test donors, or calibrators prepared according to the above techniques, were added to the plate wells in duplicate and incubated for 1 hour at room temperature with shaking at 200 rpm. The samples were then aspirated, the wells washed three times with buffer (8.7 g/L NaCl, 2.4 g/L Tris, 0.5 mL/L Tween 20, pH 7.6), followed by addition of 100 µL of $GAD_{65}$-Bi diluted in HSB (400 µg/L) prepared according to the above techniques and incubation for 1 hour at room temperature, with shaking at 200 rpm. After the incubation the contents of the wells were aspirated and wells washed three times with buffer (8.7 g/L NaCl, 2.4 g/L Tris, 0.5 m/L Tween 20, pH 7.6). Thereafter, 100 µL of a streptavidin horseradish peroxidase conjugate diluted to 1 µg/mL was added and incubated for 20 minutes at room temperature, with shaking at 200 rpm. After aspiration, the wells were washed three times with buffer (8.7 g/L NaCl, 2.4 g/L Tris, 0.5 mL/L Tween 20, pH 7.6) and once with water. 100 µL of tetramethyl benzidine was then added and incubated for 20 minutes in the dark, followed by addition of 50 µL of 0.5 mol/L $H_2SO_4$. The absorbance of the wells was then measured in an ELISA plate reader at 450 nm or in the case of samples giving an OD 450 nm>4.0, absorbance was also measured at 405 nm.

The above procedures were applied to IA-2 autoantibodies and also to the combined detection of $GAD_{65}$ and IA-2 autoantibodies (in particular, involving the preparation of IA-2 labelled with biotin, IA-2-Bi). Reference preparations of IA-2 autoantibodies for generation of a calibration curve were prepared from polyclonal IA-2 autoantibodies.

Results

Figure 1B:
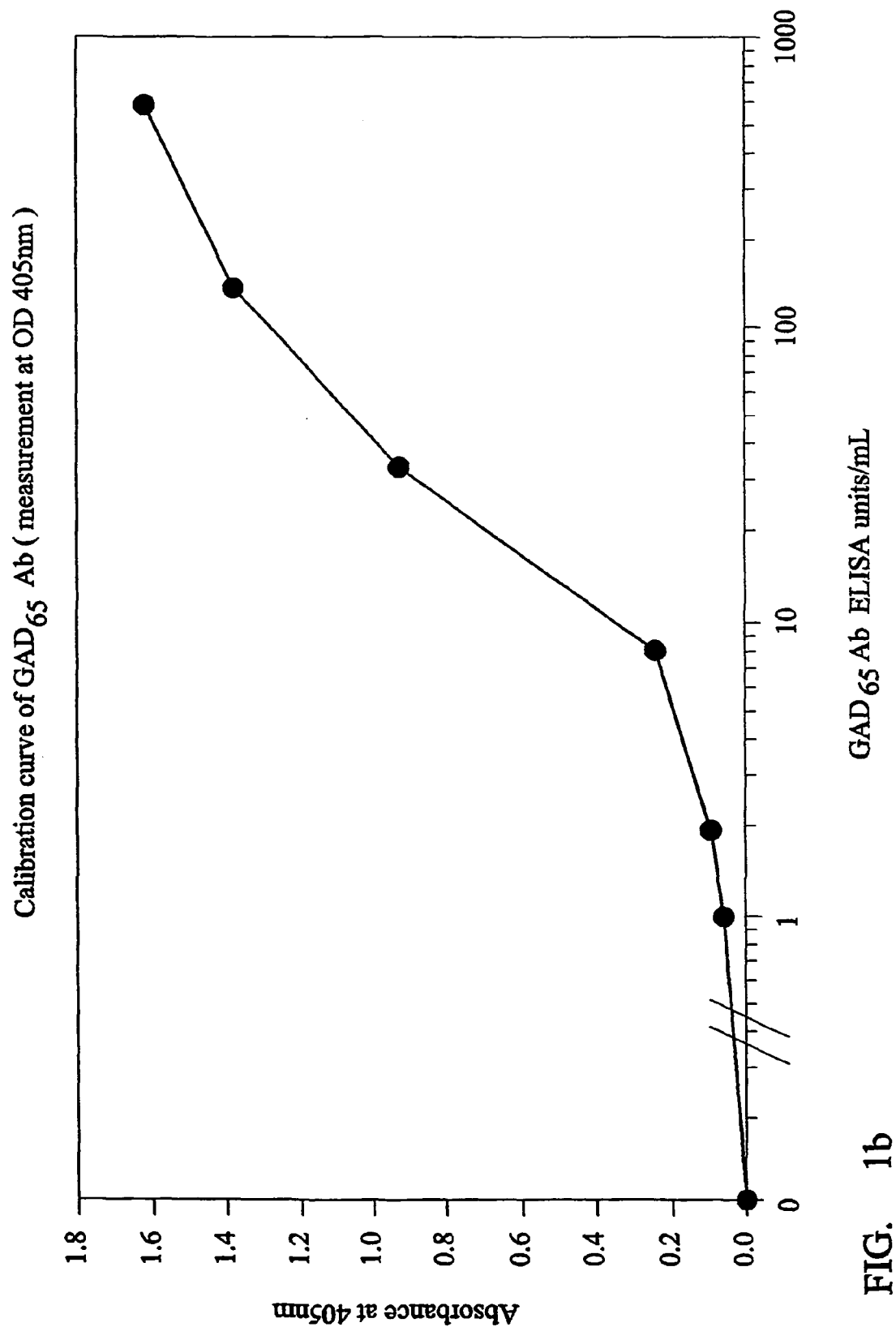

A typical calibration curve for $GAD_{65}$ obtained at OD 450 nm is shown in FIG. 1a. Seven calibrators of arbitrarily assigned $GAD_{65}$ autoantibody ELISA units from 0 ELISA units/mL to 512 ELISA units/mL were included. OD 450 nm values for the calibrators were 0.033, 0.168, 0.310, 1.020, 3.187, >4.0 and >4.0 for calibrators 0, 1.0, 2.0, 8.0, 32, 128 and 512 respectively. OD 405 nm values were 0.008, 0.048, 0.090, 0.290, 0.929, 1.385 and 1.620 for calibrators 0, 1.0, 2.0, 8.0, 32, 128 and 512 respectively as shown in FIG. 1b. Consequently, samples that gave OD 450 nm values >4.0 could be measured within the calibration curve range at OD 405 nm as shown in FIG. 1b. The mean ±SD absorbance at 450 nm for n=25 sera from healthy blood donors was 0.04±0.015.

Results of $GAD_{65}$ autoantibody measurement according to the present invention are shown in Tables 1 and 2. Results of $GAD_{65}$ autoantibodies in sera from n=18 patients with type 1 diabetes mellitus and n=14 patients with Graves' disease are shown in Table 1. All 18 diabetic sera were positive for $GAD_{65}$ autoantibodies when ELISA based techniques according to the present invention were employed (levels >1.0 ELISA units/mL), however only 13 of these patients were positive in radioimmunoassay (RIA). The 5 samples which were negative in RIA showed low levels of $GAD_{65}$ autoantibodies in ELISA based techniques according to the present invention with OD 450 nm between 0.117 to 0.980 (1.3 to 10.7 ELISA units/mL). In the case of samples with low levels in RIA (1.0 to 7.5 RIA units/mL), the OD 450 nm values in ELISA based techniques according to the present invention were between 0.290 and 1.060 (12.0 to 105.8 ELISA units/mL). In the case of samples with higher levels of $GAD_{65}$ autoantibodies in RIA (26.8 to 118.8 RIA units/mL), OD 450 nm in ELISA based techniques according to the present invention were very high >4.0 (>128 ELISA units/mL) and, therefore, the relationship between the $GAD_{65}$ autoantibody levels in the sample and the calibration curve was calculated after measurement at 405 nm. Preincubation of test sera with non-labelled $GAD_{65}$ (at final concentration from 0.0005 to 0.0µg/mL) prior to performing the ELISA resulted in a dose dependent reduction of OD 450 nm values. These experiments confirmed the specificity of the $GAD_{65}$ autoantibody ELISA based techniques according to the present invention.

In the case of n=14 sera from patients with Graves' disease, OD 450 nm values for all samples were below 0.05 (<1 ELISA unit/mL in ELISA based techniques according to the present invention); all these samples were negative for $GAD_{65}$ autoantibodies in RIA (<1 RIA unit/mL).

Comparison of the lowest detection limit for $GAD_{65}$ autoantibodies in ELISA based techniques according to the present invention and RIA is shown in Table 2. In the RIA dilutions of WHO reference preparation for islet cell autoantibodies [NIBSC 97/550] from 250 to 31.25 WHO units/mL, detectable levels of $GAD_{65}$ autoantibodies were seen. However, in the ELISA based techniques according to the present invention, $GAD_{65}$ autoantibodies were detectable in the case of WHO standard dilutions from 250 to 3.91 WHO units/mL. Further, an example of the dilution profile of a serum sample Z (from a patient with high levels of $GAD_{65}$ autoantibodies) is shown in Table 2. In the case of RIA, $GAD_{65}$ autoantibodies were detectable in the sample Z in the range from 1/8 to 1/8192 dilution. In the case of ELISA based techniques according to the present-invention, $GAD_{65}$ autoantibodies were detectable in the range from 1/8 to 1/32768 dilution. Consequently, the end point dilution analyses of WHO standard and patient's serum indicated that a 4-fold to 8-fold greater dilutions were detectable in ELISA based techniques according to the present invention compared to RIA.

An example of results of IA-2 autoantibody measurement by ELISA based techniques according to the present invention is shown in Table 3. Typical OD 450 nm values for the set of IA-2 autoantibody calibrators (0, 1.0, 2.0, 4.0, 8.0, 16, 32, 64, 128 ELISA units/mL) were from 0.054 to >4.0 and OD405 values were from 0.008 to 1.874. Sera from n=10 patients with type 1 diabetes mellitus who had IA-2 autoantibody levels in RIA from 2.0 to 38.9 RIA units/mL were all positive in ELISA based techniques according to the present invention. These samples gave OD 450 nm values between 0.209 to >4.0 (2.6 to >32 ELISA units/mL). WHO standard was detectable in IA-2 autoantibody RIA at 250 WHO units/mL and 125 WHO units/mL however, further dilutions (62.5 WHO units/mL and 31.25 WHO units/mL) were detectable in ELISA based techniques according to the present invention. OD 450 nm values in the case of n=10 sera from healthy blood donors (all negative for IA-2 autoantibodies in RIA) were between 0.030 and 0.071 (<1 ELISA unit/mL).

Results of a combination assay for $GAD_{65}$ autoantibodies and IA-2 autoantibodies are shown in Tables 4 and 5. Table 4 shows results of combined measurement of $GAD_{65}$ autoantibodies and IA-2 autoantibodies in ELISA based techniques according to the present invention, when IA-2-Bi or $GAD_{65}$-Bi or IA-2-Bi plus $GAD_{65}$-Bi were used in the assay. In the case of IA-2 autoantibody calibrators, no signal in the ELISA based techniques according to the present invention was detected when $GAD_{65}$-Bi was used, whereas dose dependent increase of OD 450 nm was observed when IA-2-Bi or IA-2-Bi plus $GAD_{65}$-Bi were used. The OD 450 nm signal with IA-2-Bi alone was essentially the same as signal with IA-2-Bi plus $GAD_{65}$-Bi. In the case of $GAD_{65}$ autoantibody calibrators, no signal was detected when IA-2-Bi was used in the assay while dose dependent response of OD 450 nm was observed with $GAD_{65}$-Bi and IA-2-Bi plus $GAD_{65}$-Bi. The OD 450 nm signals in the case of $GAb_{,65}$-Bi alone and IA-2-Bi plus $GAD_{65}$-Bi plus $GAD_{65}$-Bi were comparable. Measurement of both autoantibodies in different dilutions of serum sample Z showed a good agreement with the results of IA-2 autoantibodies or $GAD_{65}$ autoantibodies alone. Serum from an individual healthy blood donor or healthy blood donor pool serum gave very low OD 450 nm values from 0.006 to 0.046 irrespective of which biotinylated antigen was used. This experiment shows that in the combined assay to measure IA-2 autoantibodies and $GAD_{65}$ autoantibodies, the results are specific and reflect the presence of the two autoantibodies in the test sample.

More detailed results of the combined measurement of IA-2 autoantibodies and $GAD_{65}$ autoantibodies are shown in Table 5. Sera from patients with Type 1 diabetes were tested in the assay. IA-2 autoantibodies and $GAD_{65}$ autoantibodies were assessed in these sera by RIA; sera 1-3 were positive for both IA-2 autoantibodies and $GAD_{65}$ autoantibodies, sera 4-6 were negative for $GAD_{65}$ autoantibodies but positive for IA-2 autoantibodies, sera 7-9 were positive for $GAD_{65}$ autoantibodies but negative for IA-2 autoantibodies and sera 10-12 were negative for both IA-2 or $GAD_{65}$ autoantibodies. As shown in Table 5, in the combined assay one or the other or both autoantibodies were detected in serum samples. Furthermore, in the case of serum 6 that had borderline levels of IA-2 autoantibodies by RIA (0.9 RIA units/mL), the signal in the combined ELISA based techniques according to the present invention was clearly positive.

Additional examples of results with ELISA for $GAD_{65}$ autoantibodies, IA-2 autoantibodies and combined $GAD_{65}$ and IA-2 autoantibodies according to the present invention for different patient subgroups are shown in Tables 6, 7 and 8 respectively.

Conclusions

The above results show that the non-radioactive based techniques according to the present invention allow measurement of $GAD_{65}$ autoantibodies in test samples. The non-radioactive based techniques according to the present invention can also be employed to measure IA-2 autoantibodies separately or simultaneously. The measurements are specific and they are in agreement with the results of $GAD_{65}$ autoantibodies and IA-2 autoantibodies measurements by established radioactive reference methods (M Powell, L Prentice, T Asawa, R Kato, J Sawicka, H Tanaka, V Petersen, A Munkley, S Morgan, B Rees Smith, J Furmaniak. Clinica Chimica Acta, 1996 256: 175-188; and M Masuda, M Powell, S Chen, C Beer, P Fichna, B Rees Smith, J Furmaniak. Autoantibodies to IA-2 in insulin-dependent diabetes mellitus. Measurements with a new immunoprecipitation assay. Clinica Chimica Acta, 2000 291: 5366). Furthermore, measurements of $GAD_{65}$ autoantibodies and IA-2 autoantibodies by non-radioactive based techniques according to the present invention are at least as sensitive compared to results by RIA (Tables 1, 2 and 3).

The techniques according to the present invention provide a non-radioactive assay to measure $GAD_{65}$ autoantibodies or IA-2 autoantibodies with a high sensitivity that is convenient to use for diagnostic and screening purposes. A combination assay for $GAD_{65}$ and IA-2 autoantibodies according to the present invention can be of particular benefit for use in large population screening programmes.

TABLE 1

$GAD_{65}$ autoantibodies in patient sera in ELISA according to the present invention and radioimmunoassay (RIA) based on $^{125}$I-labelled $GAD_{65}$

| Sample | ELISA ELISA units/mL | OD450 nm | OD405 nm | RIA RIA units/mL |
|---|---|---|---|---|
| Serum Samples Type I DM | | | | |
| 1 | 10.7 | 0.980 | 0.254 | <1.0 |
| 2 | 8.1 | 0.660 | 0.158 | <1.0 |
| 3 | 2.1 | 0.183 | 0.024 | <1.0 |
| 4 | 1.3 | 0.117 | 0.001 | <1.0 |
| 5 | 4.4 | 0.432 | 0.091 | <1.0 |
| 6 | >128 | >4.0 | 2.100 | 74.3 |
| 7 | >128 | >4.0 | 2.283 | 118.8 |
| 8 | >128 | >4.0 | 2.155 | 83.2 |
| 9 | >128 | >4.0 | 2.230 | 87.4 |
| 10 | >128 | >4.0 | 2.023 | 83.0 |
| 11 | >128 | >4.0 | 1.774 | 41.9 |
| 12 | >128 | >4.0 | 1.554 | 26.8 |
| 13 | 105.8 | 3.596 | 1.060 | 7.5 |
| 14 | 21.9 | 1.830 | 0.485 | 3.6 |
| 15 | 20.2 | 1.735 | 0.466 | 3.1 |
| 16 | 12.0 | 1.116 | 0.290 | 1.5 |
| 17 | 43.4 | 2.615 | 0.732 | 4.7 |
| 18 | 20.8 | 1.771 | 0.473 | 2.2 |
| Serum Samples - Graves' | | | | |
| 1 | <1.0 | 0.015 | | <1.0 |
| 2 | <1.0 | 0.019 | | <1.0 |
| 3 | <1.0 | 0.049 | | <1.0 |
| 4 | <1.0 | 0.048 | | <1.0 |
| 5 | <1.0 | 0.008 | | <1.0 |
| 6 | <1.0 | 0.031 | | <1.0 |
| 7 | <1.0 | 0.036 | | <1.0 |
| 8 | <1.0 | 0.033 | | <1.0 |
| 9 | <1.0 | 0.029 | | <1.0 |
| 10 | <1.0 | 0.037 | | <1.0 |
| 11 | <1.0 | 0.036 | | <1.0 |
| 12 | <1.0 | 0.042 | | <1.0 |
| 13 | <1.0 | 0.041 | | <1.0 |
| 14 | <1.0 | 0.047 | | <1.0 |

Footnote:
GAD Ab levels above 1 RIA unit/mL were considered positive by RIA.
Type 1 DM = Type 1 diabetes mellitus.
Graves' = Graves' disease.

TABLE 2

Comparison of the sensitivity of the $GAD_{65}$ Ab measurement in ELISA and in RIA.

| Sample | ELISA ELISA units/mL | OD450 nm | OD405 nm | RIA RIA units/mL |
|---|---|---|---|---|
| WHO Standard (97/550)* | | | | |
| 250 | >128 | >4.0 | 1.234 | 6.4 |
| 125 | 45.5 | 2.670 | 0.742 | 3.6 |
| 62.5 | 17.4 | 1.557 | 0.422 | 2.5 |
| 31.25 | 10.0 | 0.894 | 0.225 | 1.1 |
| 15.63 | 4.4 | 0.431 | 0.095 | <1.0 |
| 7.81 | 2.2 | 0.202 | 0.023 | <1.0 |
| 3.91 | 1.2 | 0.100 | 0.00 | <1.0 |
| 1.95 | <1.0 | 0.058 | 0.00 | <1.0 |
| 0.98 | <1.0 | 0.031 | 0.00 | <1.0 |
| Sample Z | | | | |
| 1/8 | >128 | >4.0 | 2.048 | 91 |
| 1/32 | >128 | >4.0 | 1.868 | 76 |
| 1/128 | >128 | >4.0 | 1.769 | 38 |
| 1/512 | >128 | >4.0 | 1.591 | 13 |
| 1/1024 | 90 | 3.714 | 1.120 | 5.6 |
| 1/2048 | 29.4 | 2.542 | | 3.1 |
| 1/4096 | 12.0 | 1.375 | | 1.4 |
| 1/8192 | 6.9 | 0.784 | | 1.0 |
| 1/16384 | 2.8 | 0.385 | | <1.0 |
| 1/32768 | 1.6 | 0.210 | | <1.0 |
| 1/65536 | <1.0 | 0.132 | | <1.0 |
| 1/131072 | <1.0 | 0.092 | | <1.0 |
| 1/262144 | <1.0 | 0.055 | | <1.0 |

Footnote:
GAD Ab levels above 1 RIA unit/mL were considered positive in RIA.
*WHO units/mL.

TABLE 3

Measurement of IA-2/ICA512 autoantibodies in ELISA and in RIA based on $^{125}$I-labelled IA-2/ICA512.

| Sample | ELISA ELISA units/mL | OD450 nm | OD405 nm | RIA RIA units/mL |
|---|---|---|---|---|
| IA-2Ab Calibrator | | | | |
| 0 | | 0.054 | 0.008 | |
| 1 | | 0.114 | 0.021 | |
| 2 | | 0.183 | 0.040 | |
| 4 | | 0.313 | 0.073 | |
| 8 | | 0.614 | 0.166 | |
| 16 | | 1.219 | 0.340 | |
| 32 | | 2.506 | 0.719 | |
| 64 | | >4 | 1.371 | |
| 128 | | >4 | 1.874 | |
| Serum sample - Type 1 DM | | | | |
| 1 | >32 | >4 | 1.420 | 14.8 |
| 2 | >32 | >4 | 1.594 | 38.9 |
| 3 | 11.2 | 0.859 | 0.228 | 2.8 |
| 4 | >32 | >4 | 2.096 | 22.7 |
| 5 | >32 | >4 | 2.348 | 33.9 |
| 6 | 6.5 | 0.516 | 0.140 | 6.3 |
| 7 | >32 | >4 | 2.354 | 15.8 |
| 8 | 4.1 | 0.265 | 0.067 | 2.9 |
| 9 | 2.6 | 0.209 | 0.055 | 2.3 |
| 10 | 8.4 | 0.664 | 0.179 | 2.0 |
| WHO Standard (97/550)* | | | | |
| 250 | 18.8 | 1.503 | | 2.0 |
| 125 | 9.2 | 0.721 | | 1.2 |

TABLE 3-continued

Measurement of IA-2/ICA512 autoantibodies in ELISA and in RIA based on $^{125}$I-labelled IA-2/ICA512.

| Sample | ELISA ELISA units/mL | ELISA OD450 nm | OD405 nm | RIA RIA units/mL |
|---|---|---|---|---|
| 62.5 | 4.0 | 0.337 | | <1.0 |
| 31.25 | 2.0 | 0.191 | | <1.0 |
| 15.63 | <1.0 | 0.116 | | <1.0 |
| 7.81 | <1.0 | 0.093 | | <1.0 |
| Individual Healthy Blood Donors | | | | |
| 1 | <1.0 | 0.030 | | <1.0 |
| 2 | <1.0 | 0.036 | | <1.0 |
| 3 | <1.0 | 0.043 | | <1.0 |
| 4 | <1.0 | 0.045 | | <1.0 |
| 5 | <1.0 | 0.070 | | <1.0 |
| 6 | <1.0 | 0.045 | | <1.0 |
| 7 | <1.0 | 0.063 | | <1.0 |
| 8 | <1.0 | 0.037 | | <1.0 |
| 9 | <1.0 | 0.071 | | <1.0 |
| 10 | <1.0 | 0.069 | | <1.0 |

Footnote:
IA-2/ICA512 Ab levels above 1 RIA unit/mL were considered positive in RIA.
Type 1 DM = Type 1 diabetes mellitus.
*WHO units/mL.

TABLE 4

Combined GAD$_{65}$ Ab and IA-2/ICA512 Ab measurements in ELISA.

| Sample ELISA units/mL | IA-2-Bi OD450 nm | GAD$_{65}$-Bi OD450 nm | GAD$_{65}$-Bi + IA-2-Bi OD450 nm |
|---|---|---|---|
| IA-2 Ab Calibrator | | | |
| 8 | 1.314 | 0.022 | 1.252 |
| 16 | 2.730 | 0.033 | 2.574 |
| 32 | 3.888 | 0.031 | 3.824 |
| GAD$_{65}$ Ab Calibrator | | | |
| 4 | 0.053 | 0.460 | 0.458 |
| 16 | 0.045 | 1.518 | 1.400 |
| 32 | 0.043 | 2.033 | 2.160 |
| Serum Sample Z | | | |
| Diluted 1/2 | 3.069 | >4 | >4 |
| 1/4 | 2.328 | >4 | >4 |
| 1/8 | 0.905 | >4 | >4 |
| 1/16 | 0.401 | 3.936 | 3.875 |
| 1/32 | 0.197 | 3.379 | 3.626 |
| 1/64 | 0.143 | 2.209 | 2.512 |
| 1/128 | 0.069 | 1.718 | 1.571 |
| Individual Healthy Blood Donor Serum | 0.019 | 0.006 | 0.023 |
| Healthy Blood Donor Serum Pool | 0.022 | 0.015 | 0.046 |

TABLE 5

Combined GAD$_{65}$ Ab and IA-2/ICA512 Ab measurements in ELISA.

| Sample ELISA units/mL | OD450 nm | OD405 nm | GAD$_{65}$ Ab RIA RIA units/mL | IA-2/ICA512 Ab RIA RIA units/mL |
|---|---|---|---|---|
| GAD$_{65}$ Ab Calibrator | | | | |
| 0 | 0.080 | 0.028 | | |
| 2 | 0.231 | 0.070 | | |
| 8 | 0.737 | 0.219 | | |
| 16 | 1.476 | 0.436 | | |
| 32 | 2.117 | 0.613 | | |
| 64 | 2.648 | 0.755 | | |
| 128 | 3.607 | 1.083 | | |
| IA-2 Ab Calibrator | | | | |
| 0 | 0.065 | 0.025 | | |
| 2 | 0.205 | 0.054 | | |
| 4 | 0.308 | 0.081 | | |
| 8 | 0.552 | 0.154 | | |
| 16 | 1.116 | 0.327 | | |
| 32 | 2.031 | 0.590 | | |
| 64 | 3.596 | 1.079 | | |
| 128 | >4 | 1.777 | | |
| Serum samples - type 1 DM | | | | |
| 1 | >4 | 1.646 | 10.8 | 14.8 |
| 2 | >4 | 1.964 | 50.2 | 39.0 |
| 3 | 1.640 | 0.481 | 3.1 | 2.8 |
| 4 | >4 | 1.927 | Neg | 22.7 |
| 5 | >4 | 2.428 | Neg | 39.9 |
| 6 | 0.298 | 0.100 | Neg | 0.9 |
| 7 | 3.594 | 1.063 | 26.8 | Neg |
| 8 | >4 | 2.092 | 253.0 | Neg |
| 9 | 1.874 | 0.554 | 2.2 | Neg |

TABLE 5-continued

Combined $GAD_{65}$ Ab and IA-2/ICA512 Ab measurements in ELISA.

| Sample ELISA units/mL | OD450 nm | OD405 nm | $GAD_{65}$ Ab RIA RIA units/mL | IA-2/ICA512 Ab RIA RIA units/mL |
|---|---|---|---|---|
| 10 | 0.068 | 0.040 | Neg | Neg |
| 11 | 0.074 | 0.029 | Neg | Neg |
| 12 | 0.066 | 0.021 | Neg | Neg |
| Healthy Blood Donor Serum Pool | 0.073 | 0.020 | Neg | Neg |

Footnote:
$GAD_{65}$ Ab levels above 1 RIA unit/mL were considered positive in RIA.
IA-2/ICA512 Ab levels above 1 RIA unit/mL were considered positive in RIA.
Type 1 DM = Type 1 diabetes mellitus.

TABLE 6

$GAD_{65}$ Ab measured in different patient groups by ELISA or radioimmunoassay (RIA) based on $^{125}$I-labelled $GAD_{65}$.

| | ELISA number positive (%) (5 units/mL or greater = positive) | RIA number positive (%) (25 units/mL or greater = positive) |
|---|---|---|
| Healthy blood donors n = 300 | 2/300 (0.7%)[1] | 3/300 (1%)[2] |
| Type 1 DM n = 39 | 39/39 (100%)[3] | 32/39 (82%)[4] |
| Type 2 DM n = 62 | 1/62 (1.6%)[5] | 0/62 (0%) |
| Graves' disease n = 88 | 2/88 (2.3%)[6] | 3/88 (3.4%)[7] |
| Hashimoto's thyroditis n = 11 | 1/11 (9%)[8] | 0/11 |
| Rheumatoid arthritis n = 10 | 0/10 | 0/10 |
| Systemic lupus erythematosus n = 10 | 1/10 (10%)[9] | 1/10 (10%)[9] |

[1]Values of samples positive in $GAD_{65}$ Ab ELISA were 11 units/mL and >500 units/mL (all units/mL are WHO 97/550). Adsorption experiments indicated the presence of specific $GAD_{65}$ Ab. The same samples were negative and 2500 units/mL in the RIA respectively.
[2]Values of samples positive in $GAD_{65}$ Ab RIA were 33, 100 and 2500 units/mL. The same samples were negative and >500 units/mL in the ELISA respectively.
[3]Range of values: 5.2-greater than 500 units/mL.
[4]Range of values: negative-3800 units/mL.
[5]Value of a sample positive in $GAD_{65}$ Ab ELISA was 40 units/mL. The same sample was negative in the RIA.
[6]Values of samples positive in $GAD_{65}$ Ab ELISA were 306 and 500 units/mL. The same samples were 354 units/mL and 1700 units/mL in the RIA, respectively.
[7]Values of samples positive in $GAD_{65}$ Ab RIA were 78, 354 and 1700 units/mL. The same samples were negative, 306 and 500 units/mL in the ELISA, respectively.
[8]Value of a sample positive in $GAD_{65}$ Ab ELISA was 24 units/ml; this sample was negative in the RIA.
[9]The same sample was positive in $GAD_{65}$ Ab ELISA and RIA with values of 15 units/mL and 30 units/mL, respectively.

TABLE 7

IA-2 Ab measured in different patient groups by ELISA or radioimmunoassay (RIA) based on $^{125}$I-labelled IA-2.

| | ELISA number positive (%) (30 units/mL or greater = positive) | RIA number positive (%) (125 units/mL or greater = positive) |
|---|---|---|
| Healthy blood donors n = 210 | 2/210 (1%)[1] | 2/210 (1%)[2] |
| Type 1 DM n = 30 | 12/30 (40%)[3] | 12/30 (40%)[4] |
| Type 2 DM n = 62 | 1/62 (1.6%)[5] | 0/62 |
| Graves' disease n = 102 | 0/102 | 0/102 |
| Rheumatoid arthritis n = 10 | 0/10 | 0/10 |
| Systemic lupus erythematosus n = 10 | 0/10 | 0/10 |

[1]Values of samples positive in IA-2 Ab ELISA were 44 units/mL and 179 units/mL (units/mL are WHO 97/550). Adsorption experiments indicated the presence of specific IA-2 Ab in these samples. The same samples were negative in the RIA.
[2]Values of IA-2 Ab positive samples in RIA were 150 units/mL and 288 units/mL. The same samples were negative in the ELISA.
[3]Range of values: 132->4000 units/mL.
[4]Range of values: 178-4508 units/mL.
[5]Value of IA-2 Ab positive sample was 101 units/mL. This sample was negative in the RIA.

TABLE 8

$GAD_{65}$ Ab ELISA, IA-2 Ab ELISA and combined $GAD_{65}$ Ab + IA-2 Ab ELISA results in different patient groups.

| | number positive (%) | | |
|---|---|---|---|
| | $GAD_{65}$ Ab ELISA | IA-2 Ab ELISA | $GAD_{65}$ Ab + IA-2 Ab ELISA |
| Type 1 DM n = 35 | 28/35[1] (80%) | 14/35[2] (40%) | 33/35[3] (94.3%) |
| Type 2 DM n = 44 | 1/44[4] (2.3%) | 1/44[5] (2.3%) | 2/44[6] (4.5%) |
| Healthy blood donors n = 73 | 2/73[7] (2.7%) | 0/73 (0%) | 2/73[8] (2.7%) |
| Graves' disease n = 20 | 0/20 (0%) | 0/20 (0%) | 0/20 (0%) |
| Rheumatoid arthritis n = 10 | 0/10 (0%) | 0/10 (0%) | 0/10 (0%) |
| Systemic lupus erythematosus n = 10 | 1/10[9] (10%) | 0/10 (0%) | 1/10[10] (10%) |

[1]Value of $GAD_{65}$ Ab for samples positive in ELISA ranged from 7.3->500 units/mL (units/mL are WHO 97/550).
[2]Values of IA-2 Ab for samples positive in ELISA ranged from 34-3613 units/mL (units/mL are WHO 97/550).
[3]All combined ELISA results were expressed as index calculated as follows:

$$\frac{OD_{450nm} \text{ of sample}}{OD_{450nm} \text{ of pool of healthy blood donor sera}};$$

values of 2.0 or greater are positive
18 sera were positive for $GAD_{65}$ Ab and negative for IA-2 Ab;

TABLE 8-continued

GAD$_{65}$ Ab ELISA, IA-2 Ab ELISA and combined GAD$_{65}$ Ab + IA-2 Ab ELISA results in different patient groups.

|  | number positive (%) | |
| --- | --- | --- |
| GAD$_{65}$ Ab ELISA | IA-2 Ab ELISA | GAD$_{65}$ Ab + IA-2 Ab ELISA | all 18 were positive in the combined ELISA.
4 sera were positive for IA-2 Ab and negative for GAD$_{65}$ Ab;
all 4 were positive in the combined ELISA
10 sera were positive for GAD$_{65}$ Ab and for IA-2 Ab;
all 10 were positive in the combined ELISA
1 serum was negative for GAD$_{65}$ Ab and for IA-2 Ab but positive in the combined ELISA
2 sera were negative in all 3 assays.
[4]GAD$_{65}$ Ab levels were 10 units/mL and IA-2 Ab were negative in the one positive sample.
[5]GAD$_{65}$ Ab were negative and IA-2 Ab levels were 76 units/mL in the one positive sample.
[6]The positive samples were the same as described in 4 and 5 (index value 7.8 and 4.8 respectively).
GAD$_{65}$ Ab ELISA, IA-2 Ab ELISA and combined GAD$_{65}$ Ab + IA-2 Ab ELISA results in different patient groups.
[7]GAD$_{65}$ Ab levels were 9 and >500 units/mL but IA-2 Ab were negative in the two positive samples.
[8]The positive samples were the same as described in 7.
The index values for these samples were: 3.6 and 55.0 respectively.
[9]GAD$_{65}$ Ab levels were 15 units/mL but IA-2 Ab were negative.
[10]The positive sample was the same as described in 9.
The index value was 6.0.

The invention claimed is:

1. A method of screening a sample of serum obtained from an animal subject for analyte autoantibodies reactive with one or more antigenic molecules selected from GAD$_{65}$, GAD$_{67}$, and IA-2, or one or more variants, analogues, derivatives or fragments thereof, said method comprising:
   (a) providing an undiluted sample of serum from said subject;
   (b) providing one or more first sources of antigenic molecules with which analyte autoantibodies when present in said sample can interact, wherein the one or more first sources of antigenic molecules are provided in an amount so as to form a monovalent intermediate complex comprising [antigenic molecule]-[analyte autoantibody] capable of forming a divalent complex with antigenic molecules of one or more second sources wherein said divalent complex comprises [antigenic molecule of said first source]-[analyte autoantibody]-[antigenic molecule of said second source];
   the one or more first sources of antigenic molecules comprising
      (i) a first source of GAD antigenic molecules selected from GAD$_{65}$, GAD$_{67}$, one or more variants, analogues, derivatives or fragments thereof and fusion molecules comprising two or more directly or indirectly fused antigenic molecules selected from GAD$_{65}$, GAD$_{67}$, IA-2 and said one or more variants, analogues, derivatives or fragments thereof and wherein at least one of said antigenic molecules of said fusion molecule comprises GAD$_{65}$, GAD$_{67}$, or one or more variants, analogues, derivatives or fragments thereof, and
      (ii) a first source of IA-2 antigenic molecules selected from IA-2, one or more variants, analogues, derivatives or fragments thereof, and fusion molecules comprising two or more directly or indirectly fused antigenic molecules selected from IA-2, GAD$_{65}$, GAD$_{67}$ and said one or more variants, analogues, derivatives or fragments thereof and wherein at least one of said antigenic molecules of said fusion molecule comprises IA-2 or one or more variants, analogues, derivatives or fragments thereof;
   (c) providing one or more second sources of antigenic molecules with which analyte autoantibodies when present in said sample of serum can interact, wherein the one or more second sources of antigenic molecules comprises
      (i) a second source of GAD antigenic molecules selected from GAD$_{65}$, GAD$_{67}$, one or more variants, analogues, derivatives or fragments thereof and fusion molecules comprising two or more directly or indirectly fused antigenic molecules selected from GAD$_{65}$, GAD$_{67}$, IA-2 and said one or more variants, analogues, derivatives or fragments thereof and wherein at least one of said antigenic molecules of said fusion molecule comprises GAD$_{65}$, GAD$_{67}$, or one or more variants, analogues, derivatives or fragments thereof, and
      (ii) a second source of IA-2 antigenic molecules selected from IA-2, one or more variants, analogues, derivatives or fragments thereof, and fusion molecules comprising two or more directly or indirectly fused antigenic molecules selected from IA-2, GAD$_{65}$, GAD$_{67}$ and said one or more variants, analogues, derivatives or fragments thereof and wherein at least one of said antigenic molecules of said fusion molecule comprises IA-2 or one or more variants, analogues, derivatives or fragments thereof;
   (d) contacting said antigenic molecules as provided by steps (b) and (c) with said sample of serum being screened, whereby analyte autoantibodies when present in said sample of serum can interact with said antigenic molecules so as to form one or more complexes comprising [antigenic molecule of said first source]-[analyte autoantibody]-[antigenic molecule of said second source], wherein said antigenic molecules of said first and second sources when present in said one or more complexes comprise, or are derived from, a common antigenic molecule, or wherein binding regions of said antigenic molecules of said first and second sources, for said analyte autoantibody, when present in said one or more complexes are present in, or are derived from, a common antigenic molecule;
   (e) prior to step (d), providing immobilising means whereby said antigenic molecule of said first source as present in a complex as formed in step (d) is immobilized to a solid support prior to step (d) by coating said solid support with said antigenic molecule of said first source;
   (f) prior to, or concurrent with, or subsequent to, step (d), providing direct or indirect detectable enzymatic label whereby said antigenic molecule of said second source as present in a complex as formed in step (d) is provided with such direct or indirect detectable enzymatic label prior to, or concurrent with, or subsequent to, step (d); and
   (g) detecting the presence of complexes formed in (d) immobilized according to (e) so as to provide an indication of analyte autoantibodies present in said sample.

2. A method according to claim 1, wherein the antigenic molecules of the first and second sources when present in said one or more complexes comprise one or more common antigenic molecules.

3. A method according to claim 2, wherein antigenic molecules of said first and second sources when present in the one or more complexes comprise either $GAD_{65}$ or $GAD_{67}$.

4. A method according to claim 1, wherein one of the antigenic molecules of the first or second source when present in the one or more complexes comprises $GAD_{65}$ or $GAD_{67}$, the other antigenic molecule when present in the one or more complexes comprises one or more variants, analogues, derivatives or fragments of $GAD_{65}$, $GAD_{67}$, with which analyte autoantibodies when present in said sample of serum can interact.

5. A method according to claim 1 wherein said undiluted sample of serum is obtained from an animal subject suspected of suffering from, susceptible to or having one or more of the following disease states—type 1 diabetes mellitus and/or stiff man syndrome, type 2 diabetes mellitus, one or more autoimmune thyroid diseases, celiac disease, one or more connective tissue diseases, adrenal autoimmunity, or a combination of two or more different autoimmune diseases.

6. A method according to claim 1, wherein said indirect enzymatic label comprises alkaline phosphatase or horse radish peroxidase.

* * * * *